US010160974B2

(12) United States Patent
Gaffen et al.

(10) Patent No.: US 10,160,974 B2
(45) Date of Patent: Dec. 25, 2018

(54) **ENGINEERED CYTOKINE- AND CHEMOKINE-EXPRESSING *CANDIDA ALBICANS* STRAINS AND METHODS OF USE**

(71) Applicants: University of Pittsburgh—Of the Commonwealth System of Higher Education, Pittsburgh, PA (US); Carnegie Mellon University, Pittsburgh, PA (US)

(72) Inventors: Sarah L. Gaffen, Pittsburgh, PA (US); Mandy J. McGeachy, Pittsburgh, PA (US); Anna R. Huppler, Milwaukee, WI (US); Aaron P. Mitchell, Pittsburgh, PA (US)

(73) Assignees: University of Pittsburgh—Of the Commonwealth System of Higher Education, Pittsburgh, PA (US); Carnegie Mellon University, Pittsburgh, PA (US)

(*) Notice: Subject to any disclaimer, the term of this patent is extended or adjusted under 35 U.S.C. 154(b) by 0 days.

(21) Appl. No.: 15/117,901

(22) PCT Filed: Feb. 10, 2015

(86) PCT No.: PCT/US2015/015235
§ 371 (c)(1),
(2) Date: Aug. 10, 2016

(87) PCT Pub. No.: WO2015/123206
PCT Pub. Date: Aug. 20, 2015

(65) Prior Publication Data
US 2017/0009245 A1   Jan. 12, 2017

Related U.S. Application Data

(60) Provisional application No. 61/938,350, filed on Feb. 11, 2014.

(51) Int. Cl.
| | |
|---|---|
| *C12N 15/81* | (2006.01) |
| *C12N 9/60* | (2006.01) |
| *C07K 14/52* | (2006.01) |
| *A61K 38/00* | (2006.01) |

(52) U.S. Cl.
CPC .......... *C12N 15/815* (2013.01); *C07K 14/521* (2013.01); *C12N 9/60* (2013.01); *C12Y 304/23* (2013.01); *A61K 38/00* (2013.01); *C07K 14/52* (2013.01)

(58) Field of Classification Search
None
See application file for complete search history.

(56) References Cited

U.S. PATENT DOCUMENTS 6,747,137 B1 * 6/2004 Weinstock ........... C12Q 1/6895
435/6.13

OTHER PUBLICATIONS

Wormley et al., Protection against Cryptococcosis by Using a Murine Gamma Interferon-Producing Cryptococcus neoformans Strain. Infection and Immunity, Mar. 2007, p. 1453-1462 vol. 75, No. 3. (Year: 2007).*
Kunigo et al., Heterologous protein secretion by Candida utilis. Appl Microbiol Biotechnol (2013) 97:7357-7368 (Year: 2013).*
Pietralla et al., Th17 Cells and IL-17 in Protective Immunity to Vaginal Candidiasis. Plos One, 2011, 6:1-11 (Year: 2011).*
Chen et al., Differential secretion of Sap4-6 proteins in Candida albicans during hyphae formation. Microbiology (2002), 148, 3743-3754. (Year: 2002).*
Barelle et al., "GFP as a Quantitative Reporter of Gene Regulation in Candida albicans," *Yeast*, vol. 21:333-340, 2004.
Conti et al., "Th17 Cells and IL-17 Receptor Signaling are Essential for Mucosal Host Defense Against Oral Candidiasis," *J. Exp. Med.*, vol. 206:299-311, 2009.
Delgado et al., "Candida albicans TDH3 Gene Promotes Secretion of Internal Invertase when Expressed in *Saccharomyces cerevisiae* as a glyceraldehyde-3-phosphate dehydrogenase-invertase Fusion Protein," *Yeast*, vol. 20:713-722, 2003.
Dubois et al., "Overexpression of *Candida albicans* Secretory Aspartyl Proteinase 2 and its Expression in *Saccharomyces cerevisiae* do not Augment Virulence in Mice," Microbiol., vol. 144:2299-2310, 1998.
Huang et al., "Requirement of Interleukin-17A for Systemic Anti-*Candida albicans* Host Defense in Mice," *J. Infect. Dis.*, vol. 190:624-631, 2004.
Johnston et al., "Engineering *Candida albicans* to Secrete a Host Immunomodulatory Factor," *FEMS Microbiol. Lett.*, vol. 346:131-139, 2013.
Lee et al., "An Analysis of the *Candida albicans* Genome Database for Soluble Secreted Proteins using Computer-Based Predictions Algorithms," *Yeast*, vol. 20:595-610, 2003.

(Continued)

*Primary Examiner* — Scott Long
*Assistant Examiner* — Arthur S Leonard
(74) *Attorney, Agent, or Firm* — Klarquist Sparkman, LLP

(57) ABSTRACT

Recombinant nucleic acid constructs for expression of heterologous cytokines or chemokines in *C. albicans*, and genetically modified *C. albicans* strains comprising the recombinant nucleic acid constructs, are described. The recombinant nucleic acid molecules include a *C. albicans* gene promoter sequence, a nucleic acid sequence encoding a *C. albicans* secreted protein signal sequence and a heterologous open reading frame (ORF) of a cytokine or chemokine gene. Also described are a method of expressing a heterologous cytokine or chemokine protein in a subject, and a method of treating or inhibiting the development of candidiasis in a subject. These methods include administering a genetically modified *C. albicans* containing a recombinant nucleic acid construct for expression of a heterologous cytokine or chemokine. Exemplary cytokines or chemokines include IL8, IL17A, CXCL1, CXCL2 and CXCL5.

16 Claims, 10 Drawing Sheets

Specification includes a Sequence Listing.

(56) References Cited

OTHER PUBLICATIONS

Schaller et al., "*Candida albicans*-Secreted Aspartic Proteinases Modify the Epithelial Cytokine Response in an In Vitro Model of Vaginal Candidiasis," *Infect. Immun.*, vol. 73:2758-2765, 2005.
Shahana et al., "Reporters for the Analysis of N-glycosylation in Candida albicans," *Fungal Genet. Biol.*, vol. 56:107-115, 2013.
Steele et al., "Cytokine and Chemokine Production by Human Oral and Vaginal Epithelial Cells in Response to *Candida albicans*," *Infect Immun.*, vol. 70:577-583, 2002.
Yano et al., "The Acute Neutrophil Response Mediated by S100 Alarmins during Vaginal *Candida* Infections is Independent of the Th17-Pathway," *PLoS ONE*, vol. 7:e46311, 2012.

\* cited by examiner

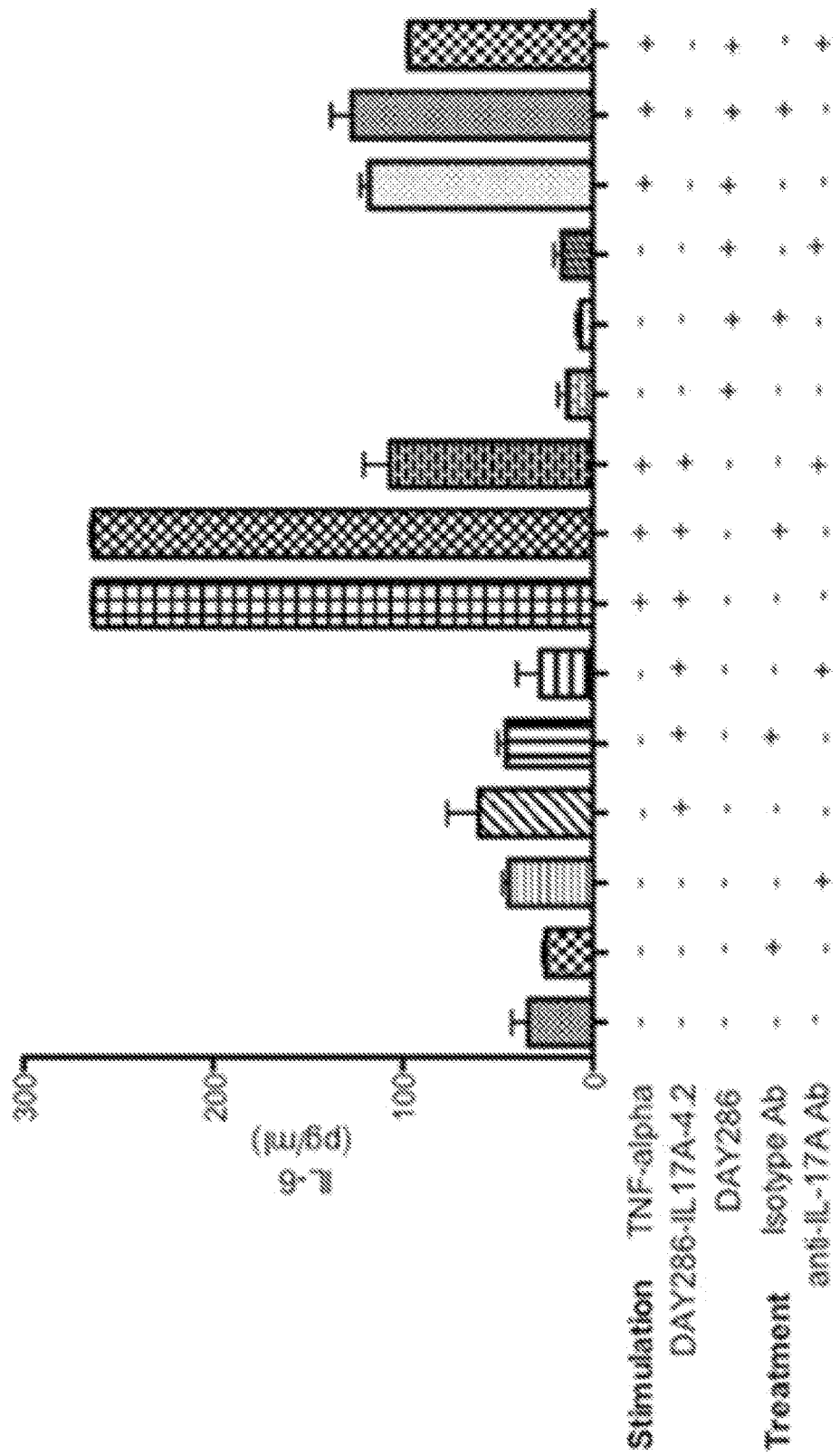

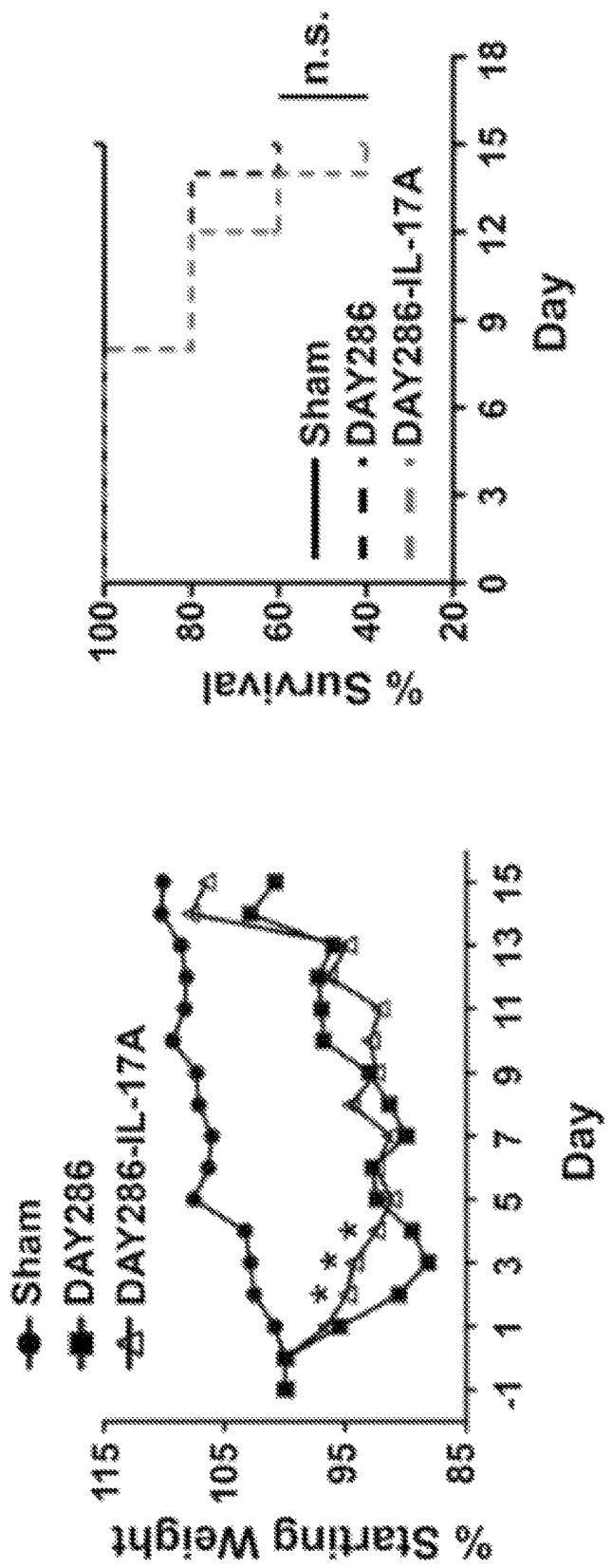

ENGINEERED CYTOKINE- AND CHEMOKINE-EXPRESSING *CANDIDA ALBICANS* STRAINS AND METHODS OF USE

CROSS REFERENCE TO RELATED APPLICATIONS

This is the U.S. National State of International Application No. PCT/US2015/015235, filed Feb. 10, 2015, published in English under PCT Article 21(2), which claims the benefit of U.S. Provisional Application No. 61/938,350, filed Feb. 11, 2014, which is herein incorporated by reference in its entirety.

ACKNOWLEDGMENT OF GOVERNMENT SUPPORT

This invention was made with government support under grant number DE022550 awarded by the National Institutes of Health. The government has certain rights in the invention.

FIELD

This disclosure concerns strains of *Candida albicans* engineered to express a cytokine or chemokine. This disclosure further concerns use of the engineered *C. albicans* strains, such as for preventing or limiting candidiasis.

BACKGROUND

Oropharyngeal candidiasis (OPC, thrush) is an opportunistic infection associated with T cell immunodeficiency, caused mainly by the commensal yeast *Candida albicans*. This organism also causes disseminated candidiasis, which is the 4$^{th}$ most common cause of hospital-acquired infections and has a 40% mortality rate. There are currently no vaccines available to any *Candida* species, or any other fungal organisms.

OPC is common in HIV/AIDS, chemotherapy, infants and the elderly, and certain congenital immunodeficiency diseases. The sensitivity of HIV patients to OPC implicates CD4+ T cells in immunity to this fungus. There are 3 subtypes of CD4+ T cells: Th1, Th2 and Th17, characterized by production of the cytokines IFNγ, IL-4 and IL-17A/IL-17F, respectively. Th17 cells are maintained by IL-23, and IL-17A/F signal through a receptor known as IL-17RA. It was previously reported that IL-17RA-/- and IL-23-/- mice are highly susceptible to OPC, whereas WT mice are resistant (Conti et al., *J. Exp. Med* 206(2):299-311, 2009).

IL-17 mediates immunity to OPC in large part by inducing expression of three CXC chemokines, CXCL1, CXCL2 and CXCL5, which help to recruit neutrophils and other myeloid cells to the oral cavity, where they facilitate clearance of the infection.

SUMMARY

Recombinant nucleic acid constructs for expression of heterologous cytokines or chemokines in *C. albicans* are provided by the present disclosure. The recombinant nucleic acid molecules include a *C. albicans* gene promoter sequence, a nucleic acid sequence encoding the signal sequence of a *C. albicans* secreted protein, and a heterologous open reading frame (ORF) of a cytokine or chemokine gene. The signal sequence is fused in frame with the heterologous ORF. In some embodiments, the recombinant nucleic acid molecules comprise the *C. albicans* TDH3 promoter sequence, a nucleic acid sequence encoding the *C. albicans* SAP5 signal sequence and a heterologous ORF of a cytokine or chemokine gene, wherein the SAP5 signal sequence is fused in frame to the heterologous ORF. Further provided are vectors comprising the recombinant nucleic acid molecules, isolated cells comprising the recombinant nucleic acid molecules or vectors, and genetically modified *C. albicans* strains comprising the recombinant nucleic acid constructs.

A method of expressing a heterologous cytokine or chemokine protein in a subject and a method of treating or inhibiting the development of candidiasis in a subject are also provided by the present disclosure. These methods include administering a genetically modified *C. albicans* containing a recombinant nucleic acid construct for expression of a heterologous cytokine or chemokine.

The foregoing and other objects, features, and advantages of the invention will become more apparent from the following detailed description, which proceeds with reference to the accompanying figures.

BRIEF DESCRIPTION OF THE DRAWINGS

FIG. 4 is a graph showing in vitro stimulation of epithelial cells with TNF-α synergy by *C. albicans* strain DAY286-IL17A-4.2. ST2 cells were stimulated for 6 hours with yeast culture supernatant from an overnight culture of strain DAY286-IL17A-4.2 or DAY286 diluted 1:10 with cell culture media. IL-17A concentration in the DAY286-IL17A-4.2 strain was 77 ng/ml by ELISA prior to dilution. Stimulation with TNF-α (1 ng/ml) was added as indicated. Treatment with anti-IL-17A Ab or isotype Ab was given as indicated. The readout for ST2 cell stimulation was IL-6 production, measured by ELISA on cell culture supernatant.

(FIG. 5A) Diagram of construct used to express IL-17A in *C. albicans*. The constitutive TDH3 promoter encoding GAPDH of *C. albicans* was used to drive expression. The Sap5 signal sequence is derived from the yeast secreted aspartyl proteinase gene, and is fused to a codon-optimized open reading frame encoding murine IL-17A without its native signal sequence. (FIG. 5B) Expression of murine IL-17A was detected by ELISA in conditioned media from two *C. albicans* clones compared to the parent *C. albicans* DAY286 strain. (FIG. 5C) The indicated *C. albicans* strains were cultured in YPD liquid culture over a 15 hour time course, and samples were analyzed for O.D. 600 (top) and plated for colony enumeration (bottom) at regular intervals.

FIGS. 7A-7E: IL-17A-secreting *Candida albicans* exhibits reduced pathogenicity in vivo early during infection. (FIG. 7A) WT mice were injected via tail with saline (Sham) or $2\times10^5$ CFU of the indicated *C. albicans* strains. After 4 days, mice were sacrificed and CFU/g kidney burden was assessed by plating. *$p=0.006$ by ANOVA and Mann-Whitney correction. (FIG. 7B) Weight loss at the indicated dates was assessed. *$p<0.05$ by ANOVA and student's t-test. (FIG. 7C) WT mice were injected as in FIG. 7A and weight loss was measured daily. *$p<0.05$ by ANOVA and student's t-test. (FIG. 7D) Survival curve of the indicated cohorts. (FIG. 7E) Fungal load at day 15 for the remaining surviving mice (n=3-4).

SEQUENCE LISTING

Figure 1:
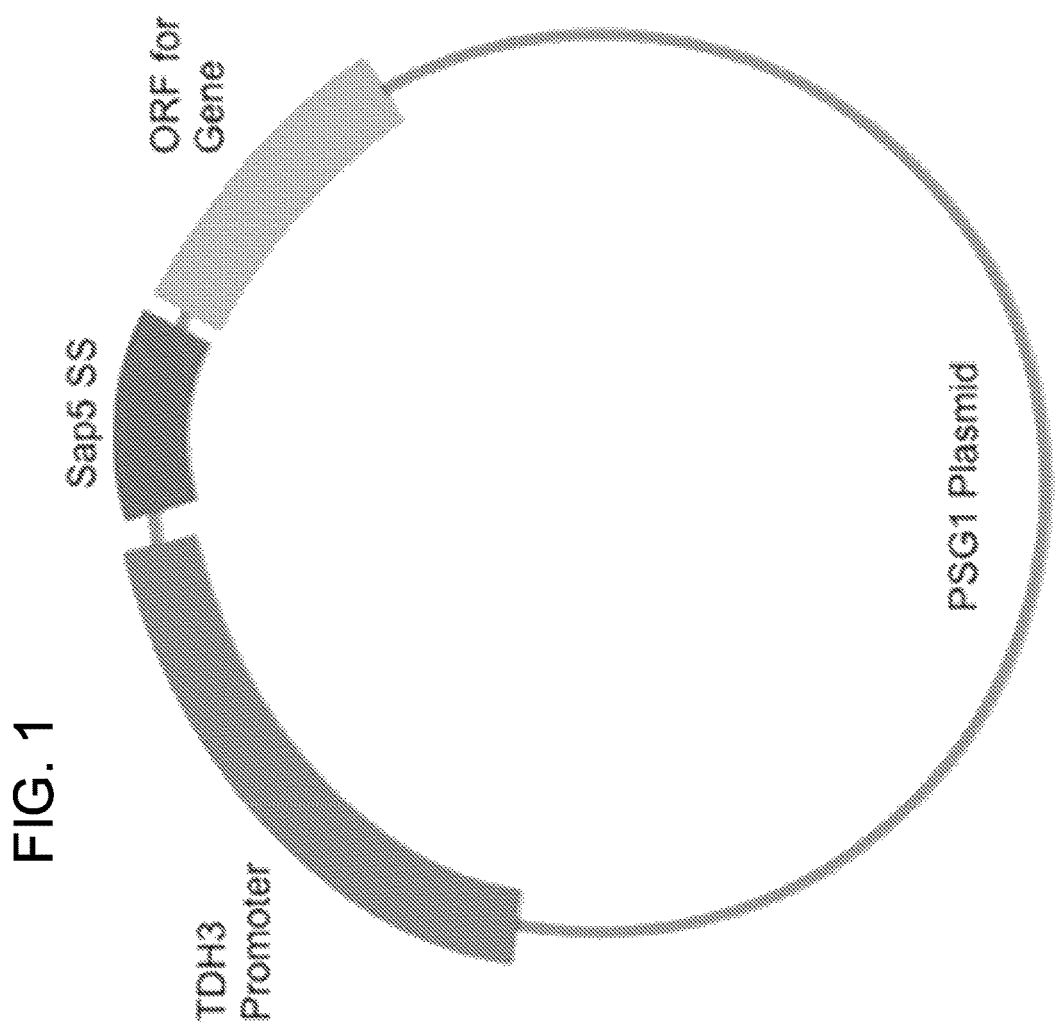
FIG. 1 is a plasmid map for constructs used to express CXCL1, CXCL2, CXCL5 or IL17A in *C. albicans*. The TDH3 promoter is a constitutive promoter from the *C. albicans* gene encoding GAPDH. Sap5 SS is the signal sequence from the *C. albicans* gene encoding secreted aspartyl proteinase. The ORF is the open reading frame for one of the four genes (CXCL1, CXCL2, CXCL5 or IL17A), adapted for expression in *C. albicans* and without the native signal sequence. All of the fragments were recombined in the PSG1 plasmid for transformation in yeast and *E. coli*.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Aug. 5, 2016, 34.2 KB, which is incorporated by reference herein. In the accompanying sequence listing:

SEQ ID NO: 1 is the nucleotide sequence of a plasmid construct for expression of CXCL1 in *C. albicans* having the following features:
nucleotides 2758-3737=TDH3 promoter
nucleotides 3758-3811=SAPS signal sequence
nucleotides 3812-4063=CXCL1 ORF optimized for expression in *C. albicans*

SEQ ID NO: 2 is the nucleotide sequence of a plasmid construct for expression of CXCL2 in *C. albicans* having the following features:
nucleotides 2758-3737=TDH3 promoter
nucleotides 3758-3811=SAPS signal sequence
nucleotides 3812-4066=CXCL2 ORF optimized for expression in *C. albicans*

SEQ ID NO: 3 is the nucleotide sequence of a plasmid construct for expression of CXCL5 in *C. albicans* having the following features:
nucleotides 2758-3737=TDH3 promoter
nucleotides 3758-3811=SAPS signal sequence
nucleotides 3812-4123=CXCL5 ORF optimized for expression in *C. albicans*

SEQ ID NO: 4 is the nucleotide sequence of a plasmid construct for expression of IL17A in *C. albicans* having the following features:
nucleotides 2758-3737=TDH3 promoter
nucleotides 3758-3811=SAPS signal sequence
nucleotides 3812-4246=IL17A ORF optimized for expression in *C. albicans*

SEQ ID NOs: 5-9 are nucleotide sequences of PCR primers.

DETAILED DESCRIPTION

I. Abbreviations
CFU colony forming units
CXCL C—X—C chemokine ligand
CXCR C—X—C chemokine receptor
ELISA enzyme linked immunosorbent assay
HIV human immunodeficiency virus
IFN interferon
IL interleukin
ORF open reading frame
PBS phosphate buffered saline
PCR polymerase chain reaction
SAP secreted aspartyl proteinase
YPD yeast-peptone-dextrose II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes. In some embodiments herein, the therapeutic agent is an engineered strain of *Candida albicans*.

*Candida albicans*: A diploid fungus that grows as both yeast and filamentous cells. *Candida albicans* is a commensal organism that is part of the normal flora in the oral cavity and gastrointestinal tract. This fungus is the causative agent of a number of opportunistic oral and genital infections in humans.

Candidiasis: A fungal infection caused by an organism of the *Candida* genus. The most common causative agent of candidiasis is the commensal yeast *Candida albicans*. Candidiasis includes superficial infections, such as oropharyngeal candidiasis (OPC; also known as thrush) and vaginitis, as well as systemic and disseminated candidiasis, which are potentially life-threatening.

Chemokines: Small cytokine proteins secreted by cells. Chemokines are capable of inducing chemotaxis in nearby responsive cells. Chemokines are classified into four main subfamilies—CXC, CC, CX3C and XC. Chemokines exert their biological effect by interacting with G protein-coupled transmembrane receptors that are found on the surface of target cells.

Chemotherapy: Treatment with a chemical agent (such as a cytotoxic agent) with therapeutic utility for treating diseases characterized by abnormal cell growth, such as tumors, neoplasms, cancer and psoriasis.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in yeast, such as the species Candida albicans. Codon optimization does not alter the amino acid sequence of the encoded protein.

Congenital immunodeficiency: An immunodeficiency that is present at birth, generally caused by a genetic defect.

CXCL1: A member of the CXC subfamily of chemokines. CXCL1 is believed to bind CXC receptor 2 (CXCR2) to recruit neutrophils. Nucleotide and amino acid sequences for CXCL2 are publically available. For example, sequences for mouse CXCL1 can be found under NCBI Gene ID 14825. The nucleotide sequence of mouse CXCL1 codon-optimized for expression in C. albicans is set forth herein as nucleotides 3812-4063 of SEQ ID NO: 1.

CXCL2: A member of the CXC subfamily of chemokines. Nucleotide and amino acid sequences for CXCL2 are publically available. For example, sequences for mouse CXCL2 can be found under NCBI Gene ID 20310. The nucleotide sequence of mouse CXCL2 codon-optimized for expression in C. albicans is set forth herein as nucleotides 3812-4066 of SEQ ID NO: 2.

CXCL5: A member of the CXC subfamily of chemokines. CXCL5 is believed to bind CXC receptor 2 (CXCR2) to recruit neutrophils. Nucleotide and amino acid sequences for CXCL5 are publically available. For example, sequences for mouse CXCL5 can be found under NCBI Gene ID 20311. The nucleotide sequence of mouse CXCL5 codon-optimized for expression in C. albicans is set forth herein as nucleotides 3812-4123 of SEQ ID NO: 3.

Cytokines: Small proteins that play an important role in cell signaling, particularly in the immune system. Cytokines are produced by a broad range of cells, including macrophages, B lymphocytes, T lymphocytes, mast cells, endothelial cells, fibroblast cells and stromal cells. Cytokines include chemokines, interferons, lymphokines, and tumor necrosis factors.

Fused in frame: The joining of two nucleic acid sequences in the same reading frame.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

Genetically modified: Refers to an organism whose genetic material has been altered, such as by the introduction of a heterologous and/or recombinant nucleic acid.

Heterologous: A "heterologous" nucleic acid sequence is a nucleic acid sequence that is derived from a different source or species. Thus, in the context of the present disclosure, a "heterologous open reading frame" is an open reading frame from a cytokine or chemokine gene that is derived from a different source or species than the C. albicans secreted protein signal sequence (e.g. a human cytokine gene ORF is heterologous to a C. albicans SAPS signal sequence). Non-limiting examples of heterologous ORFs of a cytokine or chemokine gene include mouse or human IL17A, CXCL1, CXCL2 or CXCL5.

Human immunodeficiency virus (HIV): A lentivirus that causes acquired immunodeficiency syndrome.

Immunodeficient: Lacking in at least one essential function of the immune system. As used herein, an "immunodeficient" subject (such as a human) is one lacking specific components of the immune system or lacking function of specific components of the immune system (such as, for example, B cells, T cells, NK cells or macrophages). In some cases, an immunodeficient subject comprises one or more genetic alterations that prevent or inhibit the development of functional immune cells (such as B cells, T cells or NK cells). In some examples, the genetic alteration is in IL17 or IL17 receptor.

Immunosuppressed: Refers to a reduced activity or function of the immune system. A subject can be immunosuppressed, for example, due to treatment with an immunosuppressant compound or as a result of a disease or disorder (for example, immunosuppression that results from HIV infection or due to a genetic defect). In some cases, immunosuppression occurs as the result of a genetic mutation that prevents or inhibits the development of functional immune cells, such as T cells.

Interleukin 8 (IL8): A member of the CXC chemokine family that is a major mediator of the inflammatory response. IL8 is secreted by several cell types and functions as a chemoattractant and potent angiogenic factor. Human IL8 is a functional equivalent of mouse CXCL1 and CXCL2. Nucleotide and amino acid sequences for IL8 are publically available. For example, human IL8 sequences can be found under NCBI Gene ID 3576.

Interleukin 17A (IL17A): A proinflammatory cytokine produced by activated T cells. Nucleotide and amino acid sequences for IL17A are publically available. For example, human and mouse IL17A sequences can be found under NCBI Gene ID 3605 and Gene ID 16171, respectively. The nucleotide sequence of mouse IL17A codon-optimized for expression in C. albicans is set forth herein as nucleotides 3812-4246 of SEQ ID NO: 4.

Isolated: An "isolated" biological component (such as a nucleic acid, protein or cell) has been substantially separated or purified away from other biological components (such as cell debris, other proteins, nucleic acids or cell types). Biological components that have been "isolated" include those components purified by standard purification methods.

Open reading frame (ORF): A series of nucleotide triplets (codons) coding for amino acids without any internal termination codons. These sequences are usually translatable into a peptide/polypeptide/protein/polyprotein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more engineered *Candida albicans* strains, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

SAP5: A *Candida albicans* gene encoding a secreted aspartyl proteinase. A nucleic acid sequence encoding the SAP5 signal sequence is set forth herein as nucleotides 3758-3811 of SEQ ID NO: 1. Complete mRNA and protein sequences for SAP5 are publically available (see, for example NCBI Gene ID 3639268 and Gene ID 3639155).

Secreted protein: A protein that is exported outside of a cell membrane.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Signal sequence: A short (typically 3-60 amino acids in length) peptide present at the N-terminus of newly synthesized proteins that are directed toward the secretory pathway. Signal sequences direct the post-translational transport of a protein. Signal sequences are also known as "signal peptides," "leader sequences" or "leader peptides."

TDH3 promoter: A constitutive promoter from the *C. albicans* TDH3 gene; the TDH3 gene encodes the glyceraldehyde-3-phosphate dehydrogenase (GAPDH) protein. A nucleic acid sequence encoding the TDH3 promoter is set forth herein as nucleotides 2758-3737 of SEQ ID NO: 1.

Subject: Living multi-cellular vertebrate organisms, a category that includes both human and non-human mammals, such as non-human primates.

Therapeutically effective amount: A quantity of a specified agent sufficient to achieve a desired effect in a subject being treated with that agent. For example, this may be the amount of a *Candida albicans* strain engineered to express a heterologous chemokine or cytokine for eliciting an immune response in a subject and/or for preventing infection or disease caused by *Candida albicans* (such as candidiasis). Ideally, in the context of the present disclosure, a therapeutically effective amount of an engineered *Candida albicans* is an amount sufficient to increase resistance to, prevent, ameliorate, and/or treat infection caused by *Candida albicans* (such as an opportunistic infection) in a subject without causing a substantial cytotoxic effect in the subject. The effective amount of an engineered *Candida albicans* useful for increasing resistance to, preventing, ameliorating, and/or treating infection in a subject will be dependent on, for example, the subject being treated, the manner of administration of the therapeutic composition and other factors.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Candida albicans is a commensal fungus of the human skin and mucosal surfaces. Although normally nonpathogenic, C. albicans can cause disease in settings of immunodeficiency, abdominal surgery or otherwise disrupted barriers, antibiotic use or other conditions (Romani, Nat Rev Immunol 11:275-288, 2011; Glocker and Grimbacher, Curr Opin Allergy Clin Immunol 10:542-550, 2010). By far the most serious form of candidiasis is a systemic infection characterized by fungal invasion into target organs, particularly liver, kidney and brain (Brown et al., Sci Transl Med 4:165rv113, 2012). Disseminated candidiasis is the 4$^{th}$ most common cause of hospital acquired infections and has a high mortality rate (averaging 40%) (Dongari-Bagtoglou and Fidel, J Dent Res 84:966-977, 2005).

In recent years, accumulating data has implicated the cytokine IL-17A (also known as IL-17) in immunity to Candida and other fungi (Hernández-Santos and Gaffen, Cell Host Microbe 11:425-435, 2012; Wuthrich et al., Ann Rev Immunol 30:115-148, 2012). IL-17A- and IL-17 receptor-deficient mice are highly susceptible to candidemia (Huang et al., J Infect Dis 190:624-631, 2004; van de Veerdonk et al., Shock 34:407-411, 2010; Saijo et al., Immunity 32:681-691, 2010). Similarly, humans with defects in the IL-17 pathway are especially sensitive to Candida infections, arising from mutations in genes controlling IL-17 signaling (ACT1, IL17RA, IL17RC, IL17F), genes that drive Th17 cell differentiation (DECTIN1, CARD9, STAT3, STAT1, IL12B, IL12RB), or in individuals with naturally occurring anti-IL-17 antibodies (occurring in certain thymomas and AIRE deficiency, also known as APS-1 or APECED) (Milner and Holland, Nat Rev Immunol 13:635-648, 2013; Huppler et al., Arthritis Res Ther 14:217, 2012).

Although Candida infections can be treated pharmacologically, currently available antifungal medications are limited by significant drug-drug interactions, the emergence of drug resistance and significant toxicity (Chen et al., Drugs 71:11-41, 2011; Miceli et al., Lancet Infect Dis 11:142-151, 2011). To date, there are no vaccines available to any fungal species, although an experimental vaccine to treat vaginal candidiasis is in development (Fidel and Cutler, Curr Infect Dis Rep 13:102-107, 2011; Schmidt et al., Vaccine 30:7594-7600, 2012). Experimental vaccines for Candida and other pathogenic fungi have been shown to require intact Th17 responses (Lin et al., PLoS Pathog 5:e1000703, 2009; Wuthrich et al., J Clin Invest 121:554-568, 2011). In contrast, it has been suggested that IL-17A may act directly on C. albicans to increase its virulence in a gastric model of candidiasis (Zelante et al., Nat Commun 3:683, 2012). Therefore, understanding the correlates of immunity and particularly the impact of IL-17 activity in the context of Candida infections is important in designing new drugs or preventive strategies to treat candidiasis. Accordingly, the studies disclosed herein were carried out to determine whether ectopic expression of IL-17A or other cytokines (such as IL8, CXCL1, CXCL2 and CXCL5) by Candida was protective or pathogenic in the context of disease. As described in Example 2, a yeast strain expressing murine IL-17A was generated. This strain exhibited reduced virulence during infection of a mouse model of disseminated candidiasis.

IV. Overview of Several Embodiments

Recombinant nucleic acid constructs for expression of heterologous cytokines or chemokines in C. albicans are provided by the present disclosure. The recombinant nucleic acid molecules include a C. albicans gene promoter sequence, a nucleic acid sequence encoding a signal sequence from a C. albicans secreted protein, and a heterologous open reading frame (ORF) of a cytokine or chemokine gene. The signal sequence is fused in frame with the heterologous ORF.

The promoter can be from any C. albicans gene that will provide the desired level of expression of the heterologous cytokine or chemokine. In some embodiments, the promoter is from a gene that is constitutively expressed in C. albicans, such as, but not limited to, the promoter from the TDH3, ENO1, ACT1 or MCM1 gene.

The signal sequence can be from any C. albicans secreted protein. In some embodiments, the signal sequence is from a protein encoded by any one of the following C. albicans genes: secreted aspartyl proteinase (SAP) 5, SAP1, SAP2, SAP3, SAP4, SAP6, SAP7, SAP5, SAP9, SAP10, beta-N-acetylglucosaminidase (HEX1), secretory lipase (LIP) 1, LIP2, LIP3, LIP4, LIP5, LIP6, LIP7, LIPS, LIP9, LIP10, phospholipase B1 (PLB1), PLB2, PLB3, PLB4, PLB4.5, PLB5, repressed by TUP1 protein 4 (RBT4) and RBT7.

In some embodiments, the recombinant nucleic acid molecules include the C. albicans TDH3 promoter sequence, a nucleic acid sequence encoding the C. albicans SAP5 signal sequence and a heterologous open reading frame (ORF) of a cytokine or chemokine gene. The SAP5 signal sequence is fused in frame to the heterologous ORF.

In some embodiments, the heterologous ORF is codon-optimized for expression in C. albicans. Exemplary cytokines include, but are not limited to, IL8, IL17A, CXCL1, CXCL2 and CXCL5. In some embodiments, the cytokine or chemokine gene is human IL8, human IL17A, mouse IL17A, mouse CXCL1, mouse CXCL2 or mouse CXCLS. Human IL8 is functionally equivalent to mouse CXCL1 and mouse CXCL2. Human IL17A and mouse IL17A are homologs.

In some examples of the recombinant nucleic acid molecule, the TDH3 promoter sequence comprises nucleotides 2758-3737 of SEQ ID NO: 1. In some examples, the nucleic acid encoding the SAP5 signal sequence comprises nucleotides 3758-3811 of SEQ ID NO: 1.

In some examples, the heterologous ORF is a CXCL1 ORF comprising a nucleic acid sequence at least 90%, at least 95%, at least 96%, at least 97%, at least 98% or at least 99% identical to nucleotides 3812-4063 of SEQ ID NO: 1. In other examples, the heterologous ORF is a CXCL2 ORF comprising a nucleic acid sequence at least 90%, at least 95%, at least 96%, at least 97%, at least 98% or at least 99% identical to nucleotides 3812-4066 of SEQ ID NO: 2. In other examples, the heterologous ORF is a CXCL5 ORF comprising a nucleic acid sequence at least 90%, at least 95%, at least 96%, at least 97%, at least 98% or at least 99% identical to nucleotides 3812-4123 of SEQ ID NO: 3. In yet other examples, the heterologous ORF is an IL17A ORF comprising a nucleic acid sequence at least 90%, at least 95%, at least 96%, at least 97%, at least 98% or at least 99% identical to nucleotides 3812-4246 of SEQ ID NO: 4. In particular examples, the heterologous ORF comprises nucleotides 3812-4063 of SEQ ID NO: 1; nucleotides 3812-4066 of SEQ ID NO: 2; nucleotides 3812-4123 of SEQ ID NO: 3; or nucleotides 3812-4246 of SEQ ID NO: 4.

In some examples, the recombinant nucleic acid molecule comprises a nucleic acid sequence at least 90%, at least 95%, at least 96%, at least 97%, at least 98% or at least 99% identical to nucleotides 2758-4063 of SEQ ID NO: 1; a nucleic acid sequence at least 90%, at least 95%, at least 96%, at least 97%, at least 98% or at least 99% identical to nucleotides 2758-4066 of SEQ ID NO: 2; a nucleic acid sequence at least 90%, at least 95%, at least 96%, at least 97%, at least 98% or at least 99% identical to nucleotides 2758-4123 of SEQ ID NO: 3; or a nucleic acid sequence at least 90%, at least 95%, at least 96%, at least 97%, at least 98% or at least 99% identical to nucleotides 2758-4246 of SEQ ID NO: 4. In specific non-limiting examples, the recombinant nucleic acid molecule comprises nucleotides 2758-4063 of SEQ ID NO: 1, nucleotides 2758-4066 of SEQ ID NO: 2, nucleotides 2758-4123 of SEQ ID NO: 3 or nucleotides 2758-4246 of SEQ ID NO: 4.

Further provided are vectors comprising a recombinant nucleic acid molecule disclosed herein. In some examples, the vector comprises a nucleotide sequence at least 90%, at least 95%, at least 96%, at least 97%, at least 98% or at least 99% identical to SEQ ID NO: 1, SEQ ID NO: 2, SEQ ID NO: 3 or SEQ ID NO: 4. In particular examples, the vector comprises or consists of the nucleotide sequence of SEQ ID NO: 1, SEQ ID NO: 2, SEQ ID NO: 3 or SEQ ID NO: 4.

Isolated cells comprising the recombinant nucleic acid molecules or vectors disclosed herein are further provided. In some embodiments, the isolated cells are prokaryotic cells, such as bacterial cells (e.g., *E. coli* cells). In other embodiments, the cells are eukaryotic cells, such as yeast cells (e.g., *C. albicans* cells). In some examples, the isolated cells comprise two or more recombinant nucleic acid molecules, such as two, three, four, five or six recombinant nucleic acid molecules. For example, each of the two, three, four, five or six nucleic acid constructs can express a different cytokine or chemokine.

Also provided are genetically modified *C. albicans* cells comprising a recombinant nucleic acid molecule or vector disclosed herein. In some embodiments, the recombinant nucleic acid molecule is integrated into the genome of the *C. albicans* cell. In some embodiments, the *C. albicans* cell is of a pathogenic strain of *C. albicans*, such as the DAY286 strain. In other embodiments, the *C. albicans* cell is of a non-pathogenic strain of *C. albicans*. In some examples, the genetically modified *C. albicans* cells comprise two or more recombinant nucleic acid molecules, such as two, three, four, five or six recombinant nucleic acid molecules. For example, each of the two, three, four, five or six recombinant nucleic acid constructs can express a different cytokine or chemokine.

A method of expressing a heterologous cytokine or chemokine in a subject is also provided by the present disclosure. Also provided is a method of treating or inhibiting the development of candidiasis in a subject. These methods include administering a genetically modified *C. albicans* containing a recombinant nucleic acid construct for expression of a heterologous cytokine or chemokine. Exemplary cytokines include, but are not limited to, IL8, IL17A, CXCL1, CXCL2 and CXCL5. In some embodiments, the cytokine or chemokine is human IL8, human IL17A, mouse IL17A, mouse CXCL1, mouse CXCL2 or mouse CXCL5. In some embodiments, two or more, such as two, three, four, five or six *C. albicans* strains are administered to the subject. For example, each of the two, three, four, five or six *C. albicans* strains can express a different cytokine or chemokine.

In some embodiments of the methods, the subject is human. In some embodiments, the subject is immunodeficient or immunosuppressed. The immunodeficiency or immunosuppression can be caused by any factor, such as a genetic alteration, an infection, or as the result of particular medications or therapies. In some cases, the subject has a T cell deficiency.

In some examples, the subject is infected with human immunodeficiency virus (HIV). In some examples, the subject has undergone or is undergoing chemotherapy. In other examples, the subject has a congenital immunodeficiency, such as Job's syndrome, APS-1, or a genetic defect in an IL-17 pathway component. In further examples, the subject has undergone or is undergoing treatment with an anti-cytokine biologic, such as for the treatment of autoimmunity (e.g., anti-IL-17A, anti-IL-17RA, anti-IL-23, or anti-IL-12/23p40).

Without being bound by theory, it is believed that *C. albicans* strains that secrete a heterologous cytokine or chemokine, such as IL8, IL17A, CXCL1, CXCL2 or CXCL5, bypass the need for Th17 cells or IL-17 production. For example, *C. albicans* expressing one or more of IL8, IL17A, CXCL1, CXCL2 or CXCL5 can serve as a probiotic to prevent or limit candidiasis in humans with defects in these cytokines due to, for example, T cell deficiency. Thus, the genetically modified *C. albicans* strains disclosed herein can be used to treat *Candida* infection, such as by augmenting host immunity through the secretion of cytokines or chemokines.

The following examples are provided to illustrate certain particular features and/or embodiments. These examples should not be construed to limit the disclosure to the particular features or embodiments described.

EXAMPLES

Example 1:

Engineering Chemokine- and Cytokine-expressing Candida albicans Strains

This example describes the generation and characterization of genetically modified strains of *Candida albicans* that express a heterologous chemokine (CXCL1, CXCL2 or CXCL5) or cytokine (IL17A).

Construction of *Candida albicans* Mutants

A cassette was synthesized and integrated into the *C. albicans* genome to construct a chemokine- or cytokine-secreting strain of *C. albicans*. The cassette contained a constitutive *Candida* promoter, a *Candida* signal sequence and the open reading frame (ORF) of a murine chemokine (CXCL1, CXCL2 or CXCL5) or cytokine (IL-17A). The promoter for TDH3 (the gene encoding GAPDH) was chosen due to the high level of expression in *Candida*. The first 1000 base pairs of the gene were included in the cassette. The signal sequence from *C. albicans* secreted aspartyl proteinase (the first 18 amino acids from gene SAP5) was selected to replace the signal sequence in the murine chemokines or cytokines. The ORF of CXCL1, CXCL2 or CXCL5 (minus the signal sequences) was optimized for expression in C. albicans by a commercial vendor (GeneArt from Life Technologies Corporation, Grand Island, N.Y.). The fragments were combined into a cassette in histidine-negative Saccharomyces cerevisiae by homologous recombination (gap repair) in the plasmid PSG1 (histidine positive; see FIG. 1) and grown on selective media.

The circular plasmid purified from S. cerevisiae culture was transformed into electrocompetent E. coli by electroporation. The plasmid was maintained in E. for long-term storage and purified for further characterization and integration into C. albicans. The gene cassette was verified by restriction digest (HindIII and NruI for the IL-17A cassette and KpnI and BamHI for the chemokine cassettes; Thermo Fisher Scientific Biosciences, Chicago, Ill.) and agarose gel electrophoresis to assess fragment size. The clones with the appropriate fragment sizes were confirmed with sequencing of the cassette using the following primers:

```
                                        (SEQ ID NO: 5)
GCTATGACCATGATTACGCC (SEQ ID NO: 6)
TATAATGTTTATCTAACAAAGATGTTGTGT (SEQ ID NO: 7)
GATAATGACGCAAAATTGCTTCT.
```

C. albicans strain DAY286 was transformed by lithium acetate transformation with the PSG1 plasmids containing the novel cassettes (FIG. 1). The cassettes were integrated into the C. albicans genome by recombination. Positive colonies were identified by growth on selective media and colony PCR using the following primers:

```
                                        (SEQ ID NO: 8)
GCTATGACCATGATTACGCC (SEQ ID NO: 9)
TATAATGTTTATCTAACAAAGATGTTGTGT
```

The strains were grown in YPD (yeast-peptone dextrose agar) media and stored at −80° C. in a 15% glycerol solution.
Assessment of Chemokine/Cytokine Expression/Secretion The chemokine- and cytokine-secreting C. albicans strains are assessed for chemokine expression and secretion by enzyme-linked immunosorbent assay (ELISA) of supernatants from yeast culture. The yeast strains containing the constructs are grown for 16 hours overnight in YPD media at 30° C. with agitation. The cultures are centrifuged at 2000 rpm for 5 minutes and supernatants are collected. The supernatants are serially diluted and the concentration of secreted chemokine/cytokine is measured by (ELISA) (eBioscience).

Figure 2:
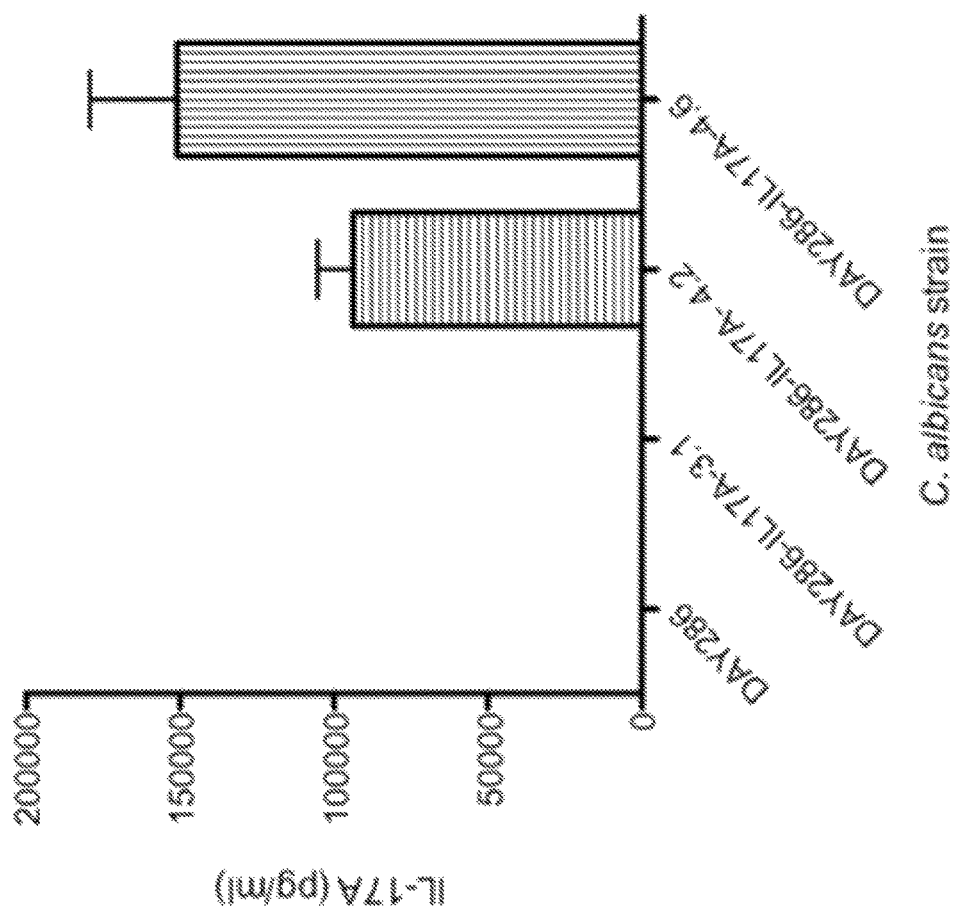
FIG. 2 is a graph showing IL-17A secretion from *C. albicans* strains by ELISA. *C. albicans* strains were grown overnight in YPD media. Culture supernatant was assessed for the concentration of secreted IL-17A by ELISA. DAY286-IL17A-4.2 and DAY286-IL17A-4.6 exhibited significant secretion of IL17A. IL17A secretion was not detected from parental strain DAY286 or from non-secreting strain DAY286-IL17A-3.1.

As shown in FIG. 2, C. albicans strains engineered to express IL17A (DAY286-IL17A-4.2 and DAY286-IL17A-4.6) exhibited significant secretion of IL17A. No IL17A secretion was detected from parental strain DAY286 or from the non-secreting strain DAY286-IL17A-3.1.
Neutrophil Migration Assay The chemokines secreted by the Candida strains were assessed for functional neutrophil chemoattraction in a transwell assay. The chemokine-secreting C. albicans strains were grown 16 hours overnight in YPD media at 30° C. with agitation. Supernatants were collected after centrifugation. Bone marrow-derived murine neutrophils were isolated using anti-Gr-1 antibodies and magnetic bead separation (Miltenyi Biotec MicroBeads and LS columns). The yeast supernatants (200 µl) were added to the lower well of a 5 µm pore-size, polycarbonate 96-well transwell plate (Corning, Lowell, Mass.) and $2.5 \times 10^5$ neutrophils (50 µl) were added to the upper chamber. To reduce the toxic effects of YPD media on murine neutrophils, yeast supernatants were diluted with RPMI media with 10% fetal bovine serum and tested in the transwell assay. The plates were incubated at 37° C. for 4-6 hours. The cellular contents of the upper and lower chambers were quantified by flow cytometry for 30 seconds at low-speed. Migration was expressed as a migration index (the ratio of cell number in the lower chamber to cell number in the upper chamber). The negative control was supernatant from DAY286 culture (the parent strain for the mutants) and the positive control was conditioned supernatants from epithelial cell culture stimulated with IL-17 and TNF-α overnight.

Figure 3:
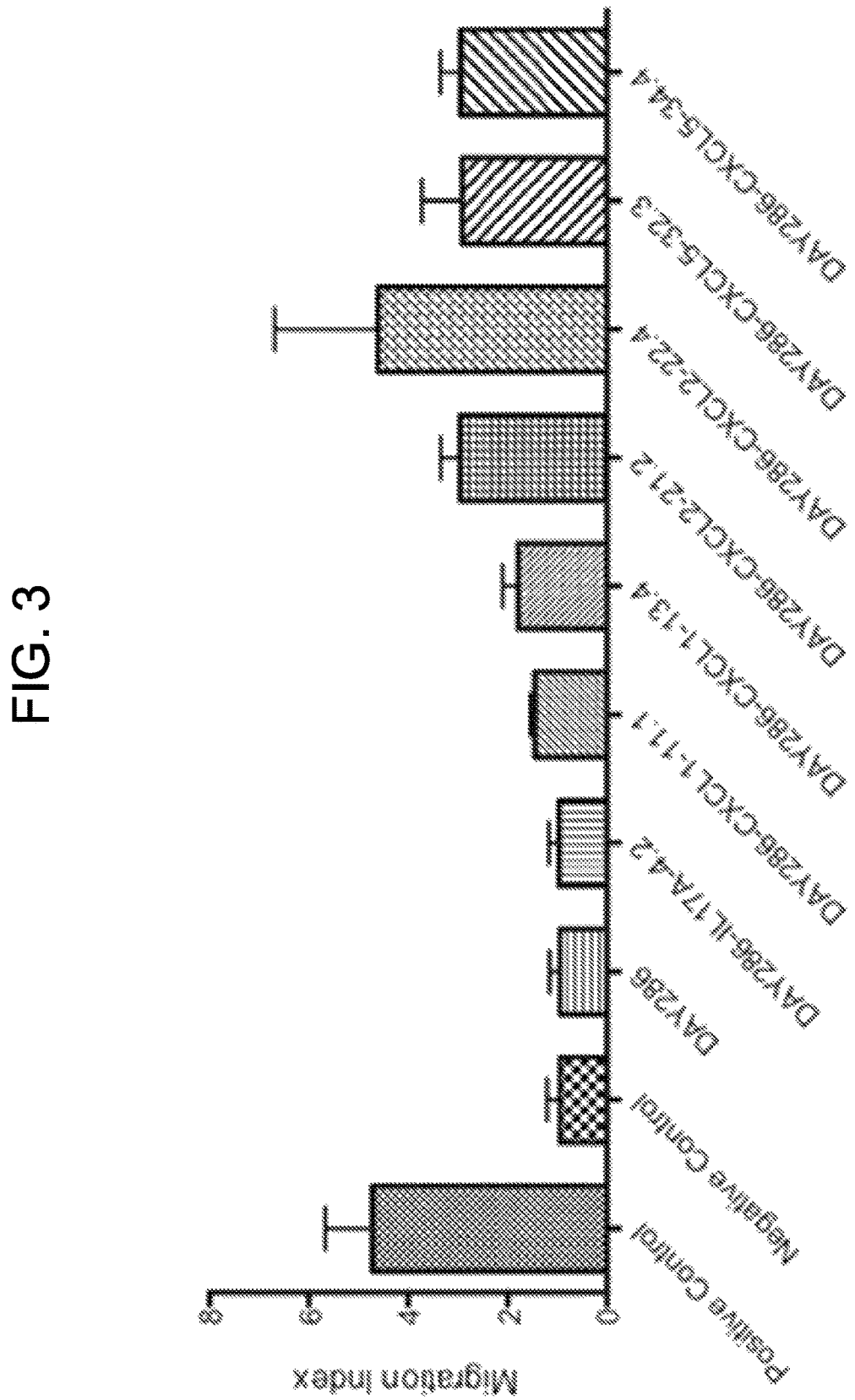
FIG. 3 is a graph showing in vitro neutrophil-recruitment by the *C. albicans* strains DAY286-CXCL2-21.2, DAY286-CXCL2-22.4, DAY286-CXCL5-32.3 and DAY286-CXCL5-34.4. Yeast strains were grown overnight in YPD media and supernatants were collected. Yeast culture supernatant (diluted 1:1 with media to prevent neutrophil toxicity) was placed in the lower chambers of a transwell plate and 2.5×10$^5$ WT neutrophils (PMN) were placed in the upper chambers. Plates were incubated for 4 hours at 37° C., followed by enumeration of PMN number in the upper and lower chambers by flow cytometry. Neutrophil migration is expressed as Migration Index (PMN lower chamber/PMN upper chamber). The positive control was conditioned supernatant from epithelial cells stimulated by IL-17A and TNF-α overnight (resulting in native chemokine secretion). The negative control was culture media.

FIG. 3 shows the results of a neutrophil recruitment assay using C. albicans strains expressing IL17A (DAY286-IL17A-4.2), CXCL1 (DAY286-CXCL1-11.1 and DAY286-CXCL1-13.4), CXCL2 (DAY286-CXCL2-21.2 and DAY286-CXCL2-22.4) or CXCL5 (DAY286-CXCL5-32.3 and DAY286-CXCL5-34.4). The positive control was conditioned supernatant from epithelial cells stimulated by IL-17A and TNF-α overnight (resulting in native chemokine secretion). The negative control was culture media. The results demonstrated that strains DAY286-CXCL2-21.2, DAY286-CXCL2-22.4, DAY286-CXCL5-32.3 and DAY286-CXCL5-34.4 induced an increase in neutrophil recruitment.
In Vitro Cell Stimulation ST2 cell stimulation was performed by plating cells with supernatant from IL-17A-secreting Candida or the parent strain DAY286 diluted 1:1 or 1:10 in serum-free AIM V media (Invitrogen, Carlsbad, Calif.) in the presence or absence of TNF-α for 4-6 hours at 37° C. Additional samples were incubated with anti-IL-17a MAb or isotype control. Supernatants were analyzed in duplicate for IL-6 production by ELISA (eBiosciences).

As shown in FIG. 4, an IL17A-secreting strain (DAY286-IL17A-4.2) and TNF-α synergistically activate epithelial cells (as evidenced by production of IL-6), an effect that is inhibited by an anti-IL17A antibody, but not by an isotype control antibody.
In Vivo Virulence Assay Mice (6-10 week old) are subjected to OPC per a standard protocol on day 0. The oral cavity is swabbed immediately before each inoculation and streaked on YPD plates to verify the absence of Candida at baseline. Mice are inoculated sublingually with a 2.5 mg cotton ball soaked with $2 \times 10^7$ colony forming units (CFU)/ml of C. albicans (strain CAF2-1, parent strain DAY286 or the chemokine/cytokine-secreting constructs) for 75 minutes under anesthesia. Weight loss and signs of illness or distress are assessed daily. Day 5 post-infection (or earlier if excessive weight loss or distress), mice are sacrificed with harvest of tongue and kidney. The organs are homogenized on a Gentle MACS Dissociator (Milenyi Biotec, Auburn, Calif.) in sterile PBS. C. albicans CFU/g tissue was assessed by plating the homogenates on YPD-ampicillin agar and colony enumeration in triplicate. Histology on tongue sections stained with periodic acid Schiff (PAS) is performed to evaluate hyphal formation and Candida invasion. Tongue sections stained with hematoxylin and eosin (H&E) are used to quantify neutrophil influx. Disseminated infection was determined by C. albicans CFU/g kidney tissue. The negative controls are subjected to sham infections (PBS) or WT C57B1/6 mice inoculated with *C. albicans*. The positive controls are immunosuppressed WT mice treated with cortisone acetate 225 mg/kg subjected to OPC.

IL-23$^{-/-}$, IL-17RA$^{-/-}$ and CXCR2$^{-/-}$ mice are subjected to OPC using the chemokine-secreting *C. albicans* mutants, the parent strain (DAY286) and strain CAF2-1 (a highly virulent strain). These KO mouse strains allow the assessment of the virulence of the chemokine-secreting C. albicans in the presence of defects downstream and upstream of the chemokines.

IL-23$^{-/-}$, Rag1$^{-/-}$ and IL-17RA$^{-/-}$ mice are subjected to OPC using the IL-17A-secreting C. albicans mutant, the parent strain (DAY286) and strain CAF2-1. These KO mouse strains allow the assessment of virulence of the IL-17A-secreting *C. albicans* strain in the presence of defects downstream and upstream of IL-17A.

Fungal burden is expressed as log10 CFU/gram of tongue or kidney tissue. Differences in fungal burden among groups are analyzed by Mann-Whitney U test. Sixteen mice per experimental group are infected, which provides an 80% power to detect a one-log difference in oral colony counts. Experiments are performed in duplicate. Control groups have 4-6 mice per experiment, and are compared to historical controls to ensure the protocol is working consistently.

Example 2:

A *Candida albicans* Strain Expressing Mammalian IL-17A Limits Pathology During Disseminated Infection

*Candida albicans* is normally a commensal fungus of the human mucosae and skin, but it causes life-threatening systemic infections in hospital settings in the face of predisposing conditions such as indwelling catheters, abdominal surgery or antibiotic use. Immunity to *C. albicans* involves various immune parameters, but the cytokine IL-17A (also known as IL-17) has emerged as a centrally important mediator of immune defense against both mucosal and systemic candidiasis. Conversely, IL-17A has been suggested to enhance the virulence of *C. albicans*, indicating that it may exert detrimental effects on pathogenesis. For the studies described below, it was hypothesized that a *C. albicans* strain expressing IL-17A would exhibit reduced virulence in vivo. A *Candida*-optimized expression cassette encoding murine IL-17A was created and transformed into the DAY286 strain of *C. albicans*. This Example demonstrates that *Candida*-derived IL-17A is indistinguishable from murine IL-17A in terms of biological activity and detection in standard ELISA assays. Expression of IL-17A does not negatively impact the growth of these strains in vitro. Moreover, the IL-17A-expressing *C. albicans* strains showed significantly reduced pathogenicity in a systemic model of *Candida* infection, which was mainly evident during the early stages of disease. Collectively, these findings show that IL-17A mitigates the virulence of *C. albicans*, and points to possible avenues for creation of probiotic agents or attenuated vaccine strains.

Materials and Methods
Plasmids, *Candida* Transformation and Culture

An expression cassette was constructed containing the first 1000 base pairs of the *Candida* TDH3 promoter, the secreted *Candida* SAP5 signal sequence and the open reading frame (ORF) of murine Il17a. The TDH3 promoter (driving yeast GAPDH) was chosen due to its high constitutive expression in yeast. The sequence of mouse Il17a was optimized for expression in *C. albicans* by GeneArt (Life Technologies, Grand Island, N.Y.) with its native signal sequence (SS) removed. The murine Il17a SS was identified by comparison to the known human IL17A SS (Fossiez et al., *J Exp Med* 183:2593-2603, 1996) and prediction software from SignalP 4.0 Server (Petersen et al., *Nat Methods* 8:785-786, 2011). To assemble the cassette, fragments were recombined into histidine-negative *Saccharomyces cerevisiae* by homologous recombination (gap repair) in the plasmid PSG1 (His+) and grown on selective media. The resulting plasmid was purified from *S. cerevisiae*, transformed into *E.* and verified by sequencing. The linearized cassette was recombined into the *C. albicans* strain DAY286 genome by lithium acetate transformation. Positive colonies were identified by growth on selective media and colony PCR using primers GCTATGACCATGATTACGCC (SEQ ID NO: 5) and TATAATGTTTATCTAACAAAGATGTT-GTGT (SEQ ID NO: 6). Strains were grown in YPD at 30° C. or stored at −80° C. in 15% glycerol.

Cell Culture and Cytokine Stimulations

ST2 stromal cells were cultured with a-MEM (Sigma, St. Louis, Mo.) with 10% FBS, L-glutamine, and antibiotics (Invitrogen, Carlsbad, Calif.). Recombinant IL-17 and TNFα were from Peprotech (Rocky Hill, N.J.) and used at 10 ng/ml and 1 ng/ml, respectively. Cells were stimulated with supernatant from IL-17A-secreting *Candida* or the parent DAY286 strain diluted 1:10 in α-MEM with 10% FBS±TNFα for 6 hours at 37° C. Additional samples were incubated with anti-IL-17A mAbs (10 µg/ml) or isotype controls (R&D Systems, Minneapolis, Minn.) starting 1 hour prior to cytokine stimulation and continuing throughout the incubation period. Supernatants were analyzed in triplicate for IL-6 and CXCL5 by ELISA. IL-6 ELISA kits were from eBioscience (San Diego, Calif.) and CXCL5 kits were from R&D Systems.

Mice and Infections

C57BL/6 female mice from The Jackson Laboratory (Bar Harbor, Me.) were used at 6-10 weeks of age. Mice were housed under a 12 hour light/dark cycle in SPF conditions and provided with autoclaved food and water ad libitum. Mice were injected in the tail vein with the indicated *Candida* strains at $2 \times 10^5$ yeast cells or sterile saline vehicle control as described (Whibley et al., *Eur J Immunol* 44:1069-1083, 2014). For injections, mice were briefly held in a commercial restraining apparatus (Braintree Scientific, Braintree Mass.). Mice were monitored visually and weighed at least once daily. Mice were humanely sacrificed by $CO_2$ inhalation at the termination of each experiment or if animals exhibited >20% weight loss or showed signs of pain or distress as delineated by the approved animal protocol. All efforts were made to minimize suffering. Tissues were harvested in a Miltenyi GentleMACS dissociator and plated in serial dilutions on YPD-Amp agar plates.

Results

To create a strain of *C. albicans* that secretes a form of IL-17A that can be recognized in vivo, a recombinant cassette composed of a constitutive *Candida albicans* TDH3 promoter (which regulates the *C. albicans* GAPDH gene) driving the murine Il17a gene (FIG. 5A) was synthesized. The native signal sequence (SS) of Il17a was replaced by the SS of the fungal secreted aspartyl proteinase 5 (SAP5). The IL-17A sequence was optimized for expression in *C. albicans*. These cassettes were recombined into the pSG1 plasmid with a histidine selective marker (Finkel et al., *PLoS Pathog* 8:e1002525, 2012). The plasmid was transformed into *C. albicans* strain DAY286 (Davis et al., *Genetics*

162:1573-1581, 2002), positive colonies were identified by growth on selective media, and colony PCR was performed to verify insertion of the Il17a gene.

Figure 5B:
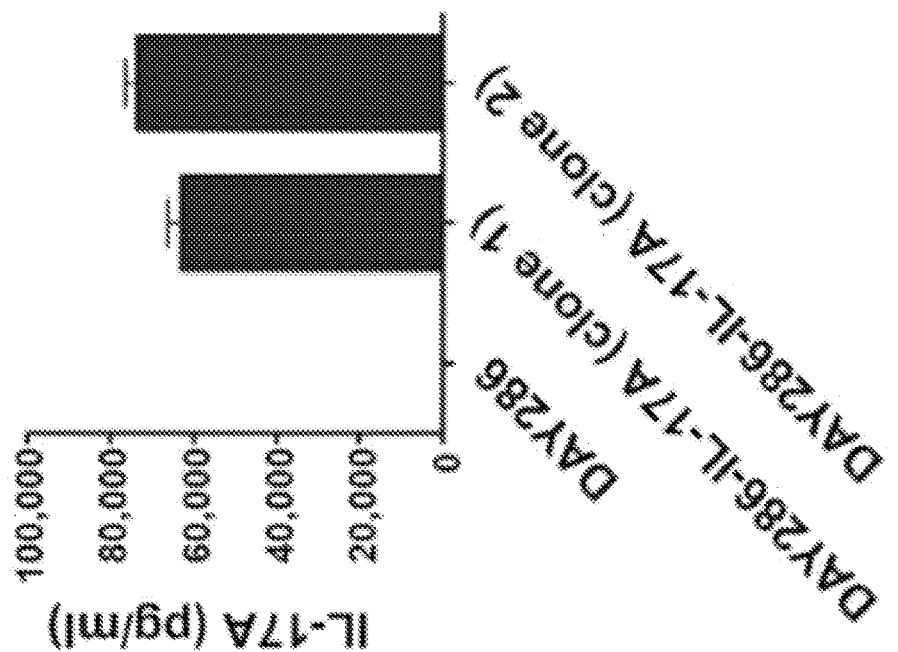
FIGS. 5A-5C: Engineering an IL-17A-secreting strain of *Candida albicans*.
Figure 5A:
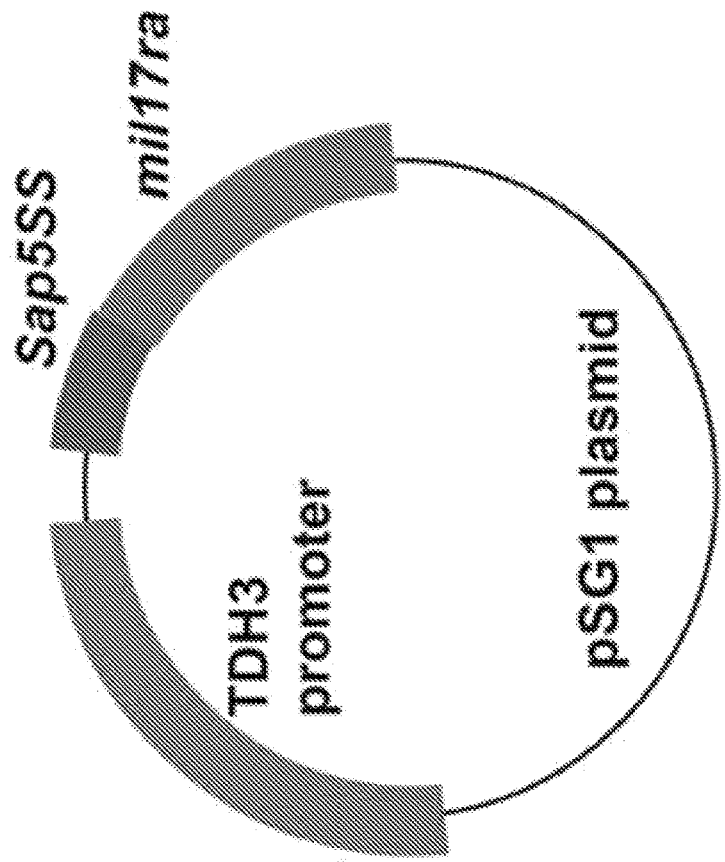
Figure 5C:
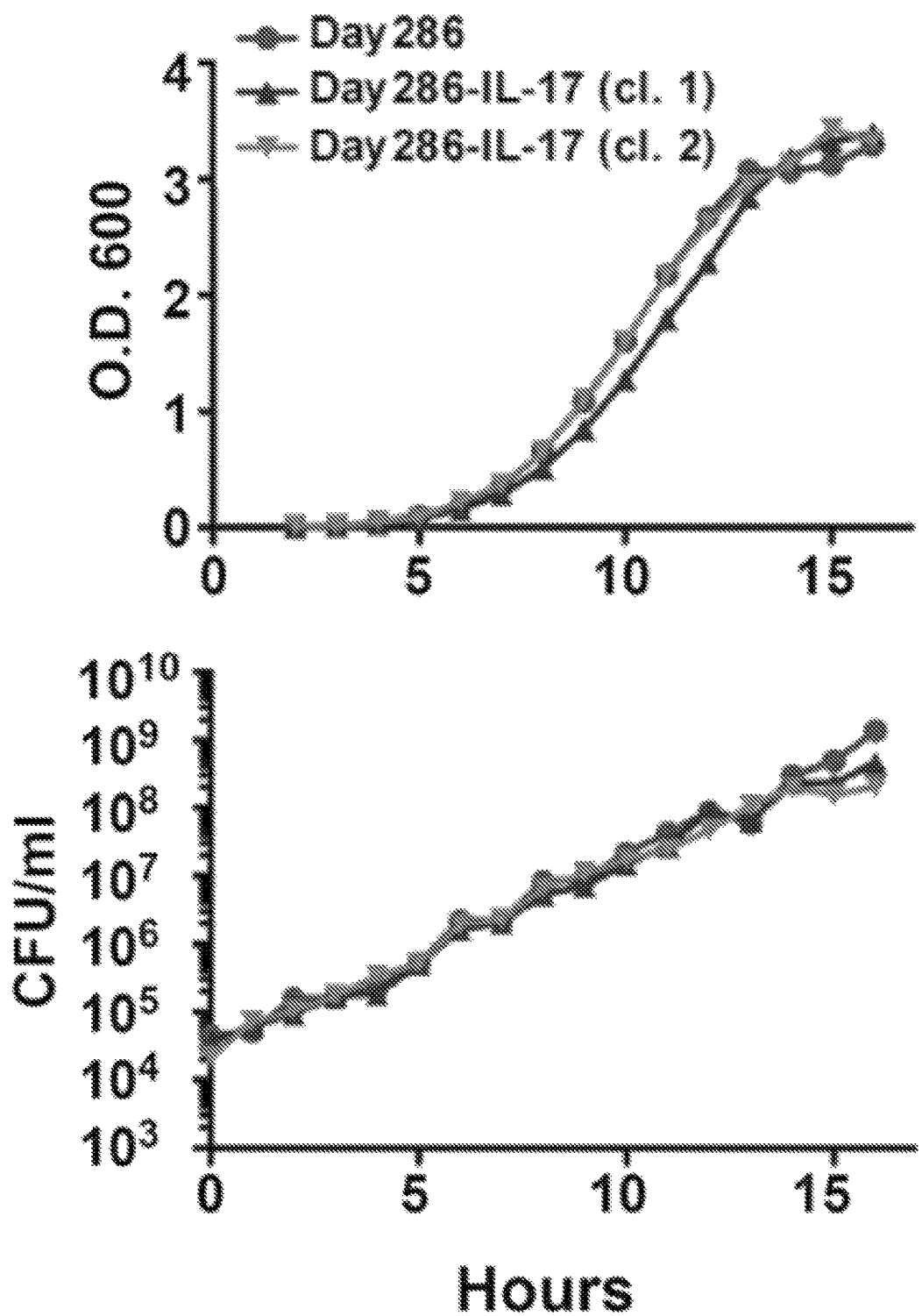

To determine whether the recombinant C. albicans strains expressed IL-17A protein, two independently derived strains of DAY286-IL-17A were cultured for 16 hours at 30° C., and conditioned supernatants were serially diluted and analyzed by ELISA. As shown, both strains exhibited substantial production of IL-17A (with a mean production of 74,829 pg/ml), whereas no IL-17A or cross-reactive contaminants were detected in the supernatant from the parent DAY286 strain (FIG. 5B). Although IL-17A has been reported to negatively impact the virulence of Candida by direct action on the fungus (Zelante et al., Nat Commun 3:683, 2012), the growth curve of IL-17A-expressing DAY286 Candida was indistinguishable from the parent strain, indicating that ectopic expression of IL-17A is not detrimental to C. albicans growth in vitro (FIG. 5C). Moreover, expression of IL-17A in the positive clones was stable over at least two months of culture. Therefore, C. albicans can express mammalian IL-17A with no apparent impact on its ability to grow or secrete this cytokine.

Figure 6A:
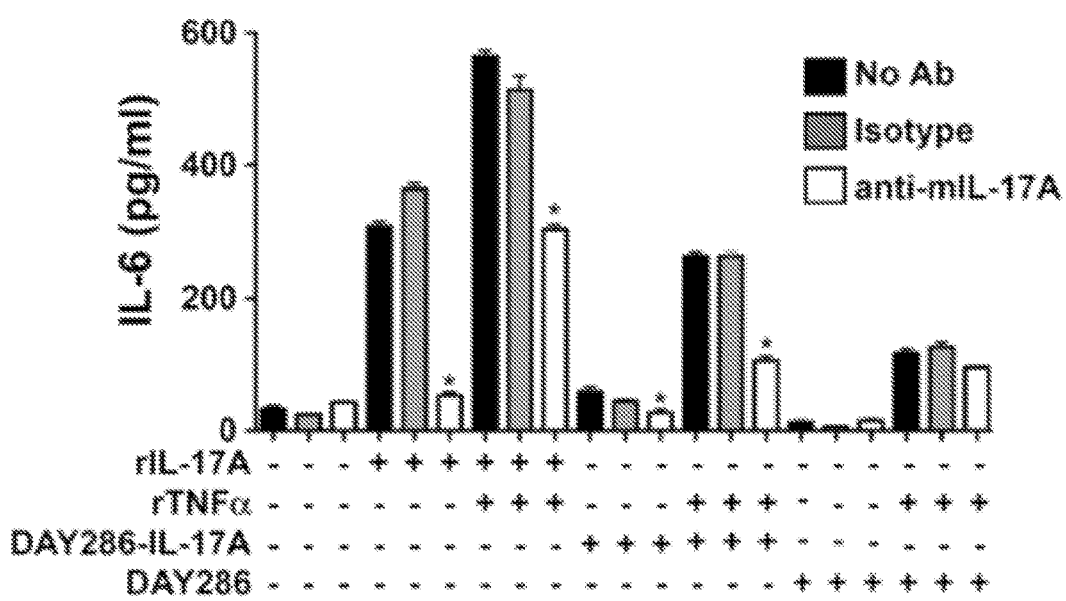
FIGS. 6A-6B: IL-17A produced by *Candida* is biologically active. Mouse ST2 cells were treated for 6 hours with recombinant IL-17A (10 ng/ml), TNFα (1 ng/ml) or a 1:10 dilution of conditioned media from DAY286 or DAY286-IL-17A (clone 2, 6-8 ng/ml concentration). The indicated samples were also treated with 10 μg/ml isotype control Ab (grey bars) or a neutralizing anti-IL-17A Ab (white bars). Supernatants were analyzed by ELISA for IL-6 (FIG. 6A) or CXCL5 (FIG. 6B).
Figure 6B:
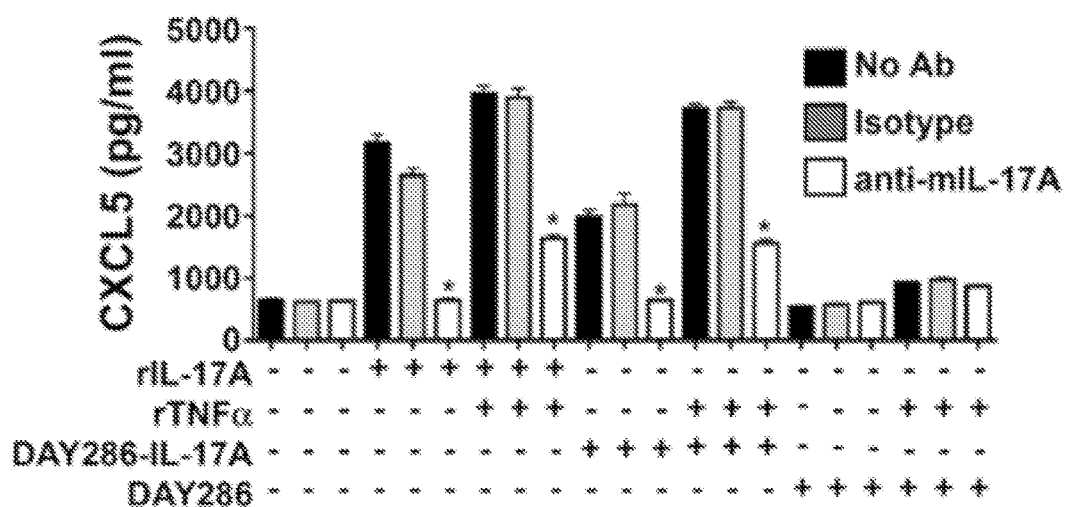

To determine whether the IL-17A produced by these Candida strains was biologically active, a mammalian cell culture assay was used to detect signaling by yeast-derived IL-17A. In mammals, IL-17A is produced predominantly by lymphocytes, but its main biological activity is on non-hematopoietic cells, particularly fibroblasts and epithelial cells. Even in these cell types, IL-17A-mediated signaling by itself is fairly modest. However, IL-17A exhibits potent signaling synergy in cooperation with TNFα to induce expression of downstream cytokines such as IL-6 (Ruddy et al., J Leukoc Biol 76:135-144, 2004; Ruddy et al., J Biol Chem 279:2559-2567, 2004). Therefore, the activity of Candida-derived IL-17 was evaluated in the presence or absence of suboptimal concentrations of TNFα using a mouse bone marrow stromal cell line, ST2, which responds to IL-17 by expressing characteristic gene products such as IL-6 and the chemokine CXCL5 (Shen et al., J Leukoc Biol 77:388-399, 2005). First, it was confirmed that recombinant murine IL-17 (10 ng/ml) and TNFα (1 ng/ml) induced IL-6 and CXCL5 in ST2 cells, which could be blocked by a neutralizing Ab against IL-17A (FIGS. 6A and 6B). It was also verified there was no effect of conditioned media from the parent DAY286 strain on ST2 cells. However, conditioned media from DAY286-IL-17A cells (diluted 1:10 to a concentration of about 6-8 ng/ml concentration of IL-17A) induced marked secretion of both IL-6 (FIG. 6A) and CXCL5 (FIG. 6B) into the ST2 cell culture supernatant. Moreover, neutralizing Abs against IL-17A, but not isotype control Abs, blocked the activity of the DAY286-IL-17A culture supernatants, demonstrating specific activity of the Candida-derived IL-17A. Thus, the IL-17A produced by C. albicans was indistinguishable from mouse IL-17A by ELISA and by its biological activity in vitro.

Figure 7B:
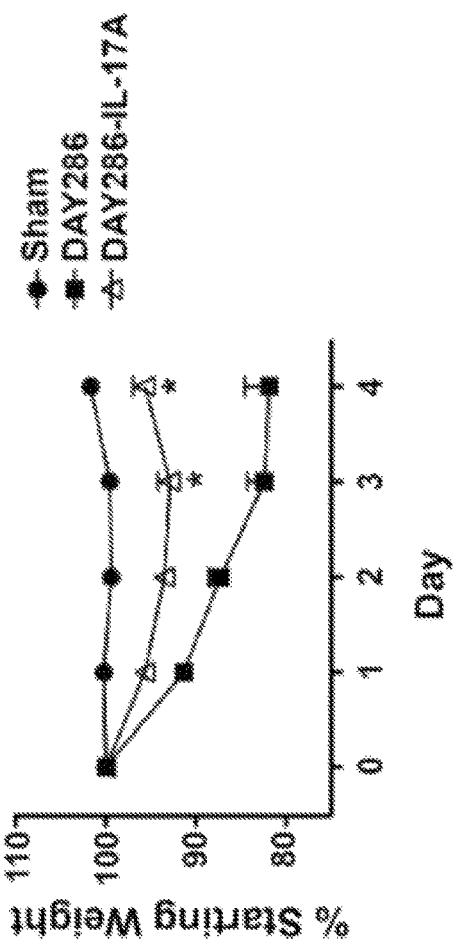
Figure 7A:
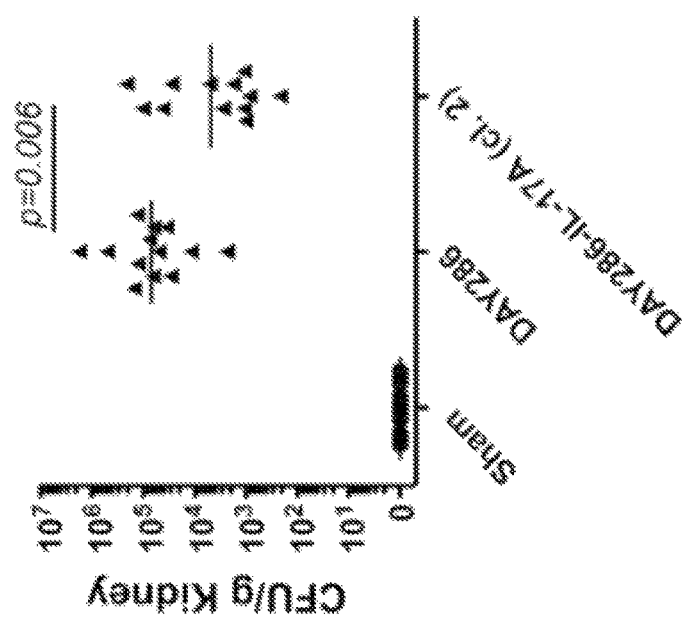

Because immunity to systemic candidiasis requires intact IL-17A signaling (Huang et al., J Infect Dis 190:624-631, 2004; van de Veerdonk et al., Shock 34:407-411, 2010), it was hypothesized that IL-17A-secreting Candida strains would be less pathogenic than the parental WT yeast strain. To test this hypothesis, WT C57BL/6 mice (n=12-13 per group) were infected intravenously with saline (Sham) or with 2×10⁵ CFU of DAY286 or DAY286-IL-17A strains. Only mice that received a successful injection (as evidenced by lack of resistance upon i.v. injection and blood flash upon needle removal) were included in the analysis. After 4 days, mice were sacrificed and kidney fungal burdens assessed by plating serial dilutions of tissue homogenate on YPD agar followed by colony enumeration in triplicate. As expected, there was no C. albicans detectable in the Sham-infected kidneys. The geometric mean of the kidney fungal load in the DAY286-infected mice was 72,202 CFU/g, whereas in the DAY286-IL-17A-infected mice the mean load was 4,895 CFU/g, representing an approximately 15-fold reduction in fungal burden (FIG. 7A). These differences were reproducible and statistically significant (p=0.006). Consistent with a decreased fungal burden, there was substantially less weight loss in the DAY286-IL-17A infected cohort compared to the DAY286-infected group (FIG. 7B). Although there is a difference in histidine biosynthesis between these strains, it has been shown that the his1 mutation does not impair pathogenicity in this model (Noble and Johnson, Eukaryot Cell 4:298-309, 2005). These data indicate that ectopic expression of IL-17A by C. albicans significantly reduces its virulence during disseminated candidiasis.

To determine whether the effect of IL-17A was long-lasting, mice were infected and weight loss and survival were tracked over a 15 day time course. Again, during the first 4 days of infection, the DAY286-IL-17A infected mice showed less pronounced weight loss compared to mice infected with the parental Day286 strain (FIG. 7C). However, starting at day 5 and continuing for the remainder of the experiment, there was no difference in weight loss between mice infected with either strain. There was also no difference in survival (FIG. 7D) or fungal burden (FIG. 7E) in the few surviving animals (n=3-4) at day 15. Therefore, the main activity of IL-17A appears to be in the early time points post-infection, with other factors coming into play at later stages of disease.

Therapeutic Applications

It is now well established that the IL-17/Th17 pathway is an essential component of the immune response to pathogenic Candida albicans infections, not only in mouse models of disease, but also in humans (Milner and Holland, Nat Rev Immunol 13:635-648, 2013). However, this subject remains controversial, as IL-17A has been reported to be pathogenic in gastrointestinal Candida infections (Zelante et al., Eur J Immunol 37:2695-2706, 2007) and may exert a direct effect on the yeast to enhance its virulence (Zelante et al., Nat Commun 3:683, 2012). Conversely, IL-17 signaling is clearly protective in other forms of candidiasis (Conti et al., J Exp Med 206:299-311, 2009; Conti et al., J Exp Med 211:2075-2084, 2014; Conti and Gaffen, Microbes Infect 12:518-527, 2010). Moreover, the mechanisms by which IL-17 exerts its effects in the context of candidiasis are not fully understood. IL-17 is essential to control the neutrophil and antimicrobial peptide responses to candidiasis (Conti et al., J Exp Med 206:299-311, 2009; Saunus et al., Front Biosci 13:5345-5358, 2008; Huppler et al., J Immunol 192:1745-1752, 2014; Conti et al., Mucosal Immunol 4:448-455, 2011). In addition, a study suggests that IL-17 may also be important for driving NK cell function in disseminated disease through a mechanism dependent on GM-CSF (Bar et al., Immunity 40:117-127, 2014).

Figure 7E:
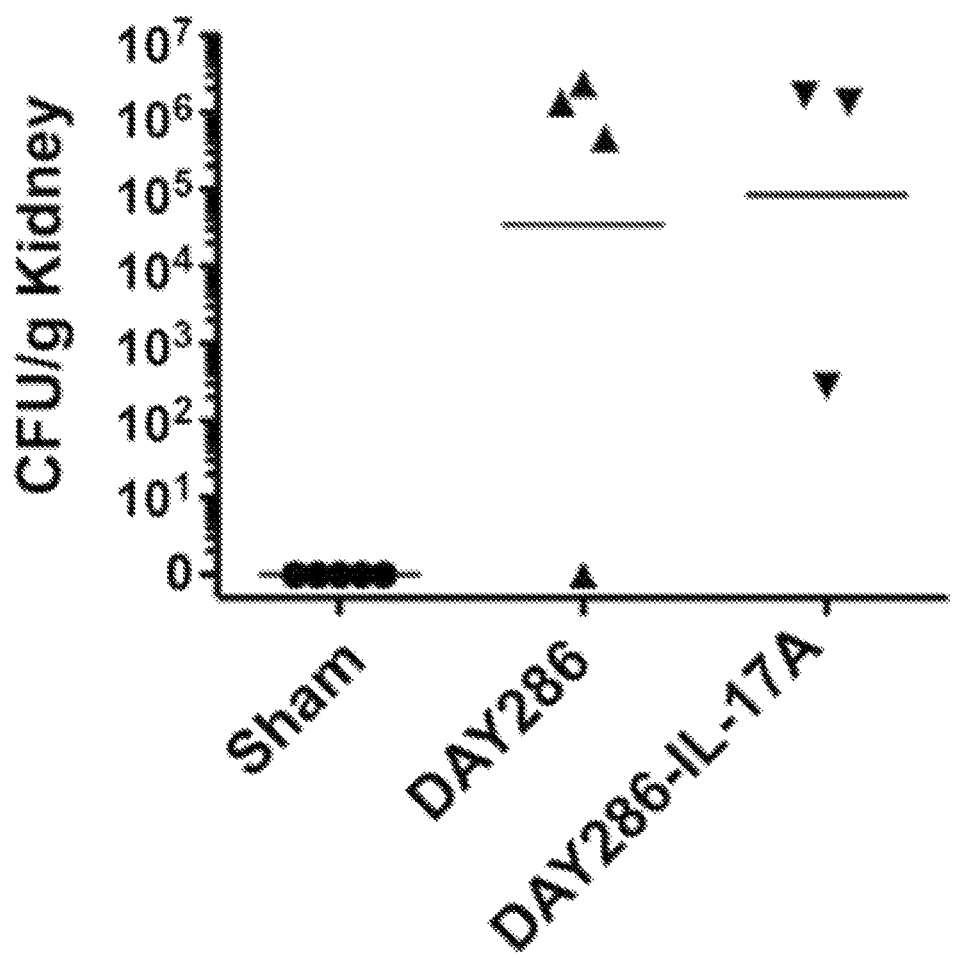

The studies disclosed herein demonstrate the effect of expressing IL-17A in Candida albicans during infection. Expression of IL-17A by the yeast did not impact its growth rate or visual appearance, indicating that even the remarkably high levels of this cytokine (>70 ng/ml) produced by these strains are not detrimental (FIG. 5C). IL-17A expression reduced the pathogenicity of the fungus in a mouse model of disease (FIG. 7A). Most of the beneficial effect is evident during the first 4 days of infection (FIGS. 7E-7F). This observation suggests that the most important impact of IL-17A occurs early during infection, but at later stages other factors may come into play. However, IL-17RA⁻/⁻ mice are not found to recover from candidiasis even in long-term settings (Huang et al., *J Infect Dis* 190:624-631, 2004; Hernández-Santos et al., *Mucosal Immunol* 6:900-910, 2013). Since IL-17RA is a common subunit that serves as an essential signaling receptor for several IL-17-family cytokines (IL-17F, IL-17A/F, IL-17C and IL-25) (Gaffen et al., *Nat Rev Immunol* 14:585-600, 2014), this finding may indicate a selective effect of IL-17A during early infection.

Ectopic expression of host immune genes has been previously used as an approach to influence virulence in fungal organisms. For example, expression of S100A8/A9 (calprotectin) in *C. albicans* was shown to stimulate chemotaxis of neutrophils, though not to alter virulence per se (Johnston et al., *FEMS Microbiol Lett* 346:131-139, 2013; Yano et al., *Infect Immun* 82:783-792, 2014). Wormley et al. expressed murine IFNγ in the fungal pathogen *Cryptococcus neoformans*, which conferred dramatic protection against secondary infection in a mouse model of disease (Wormley et al., *Infect Immun* 75:1453-1462, 2007). An intriguing translational use of *Candida* strains engineered to express immune genes is for use as a probiotics or prophylactic vaccines.

*C. albicans* is a common commensal in humans, with a 30% colonization rate of mucosal surfaces including the skin, GI tract, vaginal mucosa and oral cavity. Mucosal application of the engineered strains could be used to outcompete more pathogenic wild type strains at these sites or to induce protective immune responses against secondary exposure.

Antibodies to cytokines have revolutionized treatment for autoimmune disease. However, an inevitable risk with biologic therapies is infection (Strangfeld and Listing, *Best Pract Res Clin Rheumatol* 20:1181-1195, 2006). Antibodies to IL-17 and IL-17RA are currently in advanced clinical trials to treat autoimmunity, and have exhibited particularly good efficacy in psoriasis (Papp et al., *N Engl J Med* 366:1181-1189, 2012; Leonardi et al., *N Engl J Med* 366:1190-1199, 2012; Genovese et al., *Arth Rheum* 62:929-939, 2010; Hueber et al., *Sci Transl Med* 2:52ra72, 2010). Some patients in these trials and also individuals with naturally-occurring Abs against IL-17 (e.g. patients with autoimmune polyendocrinopathy syndrome-1 arising from A/RE-deficiency) develop OPC or chronic mucocutaneous candidiasis (CMC) (Kisand et al., *J Exp Med* 207:299-308, 2010; Puel et al., *J Exp Med* 207:291-297, 2010; Langley et al., *N Engl J Med* 371:326-338, 2014). CMC is also seen in rare individuals with mutations in genes that directly impact IL-17 signaling, including IL17RA, ACT1 or IL17F (Puel et al., *Science* 332:65-68, 2011; Boisson et al., *Immunity* 39:676-686, 2013). Although disseminated candidiasis is not typically seen in such patients, it was recently found that patients taking TNFα inhibitors to treat rheumatoid arthritis show elevated oral colonization with *C. albicans* and reduced IL-17-associated immune responses (Bishu et al., *Arth Res Ther* 16:R50, 2014). Thus, it is plausible that patients taking anti-cytokine therapies, particularly those that target the Th17/IL-17 pathway, may be at a higher risk for developing systemic candidiasis in the face of predisposing factors, such as an indwelling catheter, abdominal surgery or long-term antibiotic use.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant nucleic acid molecule comprising a *Candida albicans* (*C. albicans*) TDH3 gene promoter sequence, a nucleic acid sequence encoding a *C. albicans* secreted aspartyl proteinase 5 (SAP5) protein signal sequence and a heterologous open reading frame (ORF) of a cytokine or chemokine gene, wherein the cytokine or chemokine gene is a human or mouse interleukin 17A (IL17A) gene, a human IL8 gene, a mouse C—X—C chemokine ligand 1 (CXCL1) gene, a mouse CXCL2 gene or a mouse CXCL5 gene, and wherein the nucleic acid encoding the SAP5 signal sequence is fused in frame to the heterologous ORF.

2. The recombinant nucleic acid molecule of claim 1, wherein the heterologous ORF is codon-optimized for expression in *C. albicans*.

3. The recombinant nucleic acid molecule of claim 1, wherein the TDH3 promoter sequence comprises nucleotides 2758-3737 of SEQ ID NO: 1.

4. The recombinant nucleic acid molecule of claim 1, wherein the nucleic acid encoding the SAP5 signal sequence comprises nucleotides 3758-3811 of SEQ ID NO: 1.

5. The recombinant nucleic acid molecule of claim 1, wherein:
the heterologous ORF is a CXCL1 ORF comprising nucleotides 3812-4063 of SEQ ID NO: 1;
the heterologous ORF is a CXCL2 ORF comprising nucleotides 3812-4066 of SEQ ID NO: 2;
the heterologous ORF is a CXCL5 ORF comprising nucleotides 3812-4123 of SEQ ID NO: 3; or
the heterologous ORF is an IL17A ORF comprising nucleotides 3812-4246 of SEQ ID NO: 4.

6. The recombinant nucleic acid molecule of claim 1, comprising nucleotides 2758-4063 of SEQ ID NO: 1, nucleotides 2758-4066 of SEQ ID NO: 2, nucleotides 2758-4123 of SEQ ID NO: 3 or nucleotides 2758-4246 of SEQ ID NO: 4.

7. A vector comprising the recombinant nucleic acid molecule of claim 1.

8. The vector of claim 7, comprising the nucleotide sequence of SEQ ID NO: 1, SEQ ID NO: 2, SEQ ID NO: 3 or SEQ ID NO: 4.

9. An isolated cell comprising the recombinant nucleic acid molecule of claim 1.

10. A genetically modified *C. albicans* cell comprising the recombinant nucleic acid molecule of claim 1.

11. The genetically modified *C. albicans* cell of claim 10, wherein the recombinant nucleic acid molecule is integrated into the genome of the *C. albicans* cell.

12. A method of expressing a heterologous cytokine or chemokine in a subject, comprising administering to the subject the genetically modified *C. albicans* cell of claim 10.

13. A method of treating or inhibiting the development of candidiasis in a subject, comprising administering to the subject the genetically modified *C. albicans* cell of claim 10.

14. The method of claim 12, wherein the subject is human.

15. The method of claim 12, wherein the subject is immunodeficient or immunosuppressed.

16. The method of claim 15, wherein the subject is infected with human immunodeficiency virus (HIV), the subject has undergone or is undergoing chemotherapy, or the subject has a congenital immunodeficiency.

* * * * *

SEQUENCE LISTING

```
<160> NUMBER OF SEQ ID NOS: 9

<210> SEQ ID NO 1
<211> LENGTH: 6113
<212> TYPE: DNA
<213> ORGANISM: Artificial Sequence
<220> FEATURE:
<223> OTHER INFORMATION: Synthetic construct (CXCL1 plasmid)
<220> FEATURE:
<221> NAME/KEY: misc_feature
<222> LOCATION: (2758)..(3727)
<223> OTHER INFORMATION: TDH3 promoter
<220> FEATURE:
<221> NAME/KEY: misc_feature
<222> LOCATION: (3758)..(3811)
<223> OTHER INFORMATION: SAP5 signal sequence
<220> FEATURE:
<221> NAME/KEY: misc_feature
<222> LOCATION: (3812)..(4063)
<223> OTHER INFORMATION: Codon-optimized CXCL1 ORF

<400> SEQUENCE: 1
gacgaaaggg cctcgtgata cgcctatttt tataggttaa tgtcatgata ataatggttt      60
cttaggacgg atcgcttgcc tgtaacttac acgcgcctcg tatcttttaa tgatggaata     120
atttgggaat ttactctgtg tttatttatt tttatgtttt gtatttggat tttagaaagt     180
aaataaagaa ggtagaagag ttacggaatg aagaaaaaaa aataaacaaa ggtttaaaaa     240
atttcaacaa aaagcgtact ttacatatat atttattaga caagaaaagc agattaaata     300
gatatacatt cgattaacga taagtaaaat gtaaaatcac aggattttcg tgtgtggtct     360
```

```
tctacacaga caagatgaaa caattcggca ttaatacctg agagcaggaa gagcaagata    420
aaaggtagta tttgttggcg atcccctag agtcttttac atcttcggaa aacaaaaact    480
attttttctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaggaa gagtatgagt    720 attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg gttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc cagggggaaa cgcctggtat ctttatagtc ctgtcgggtt tcgccacctc   2280
tgacttgagc gtcgattttt gtgatgctcg tcagggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
```

```
agcggataac aatttcacac aggaaacagc tatgaccatg attacgccaa gcgcgcagta    2760
gtagtagtgg tatgatgcaa atttattgtt tgtattttt tttttgttgc tcctcgtcga    2820
caacgactgc tgattcacac caccaccacc tttgtagtca aattaaaatc gtcggtggca    2880
aaaaaaaaca cagacacaca catacagaca attgcgatat tttattttag ggtcaatttg    2940
gaacgtcacc atacagtatt cagtatgatt aatttgactt gcaaaataca aatcgcgtgg    3000
ttcaattccg aaaaattgat agtgttccat gaaaaattac aaggagagcc gtgaattata    3060
acaaatttac tcacattttg ctggcaatt tctttaaccc ccttaatttt tttcatgcag     3120
tttattattt tacgtagaag cttattctct aaacactcgg ttatccgaat atattttgct    3180
ttcagagcaa ttgactgata taataccatc aattgaataa atcagtatca tcaaatgcta    3240
gtttgagttc aataaaaggt ataatcggtg ttaactgaaa ggtattgtct aattaattag    3300
gttgcggttt ttggatcagc tgtttcaaat ccaggctcgt ggtgcacatt ttttatttt     3360 gttgtgatga ttttttcttt tctttgctta atagttagtt agtaaaatgg ataatgacgc    3420
aaaattgctt ctgaatggat gataatgccc cgggtatggc gtgtcccgta caaatcatat    3480
tatgcaaaaa tagccaaaat agacaaaaat aggtggaaat tgtttcaacc aacccactca    3540
accactaaaa tttgtcttgt caaagccaat tccaacgaaa attggatttt ttttgactta    3600
atatatatta acccttgaaa ttcccttcaa ttggaaaatt tttttaattt atttatttct    3660
tctttctttt tttcttttc ttttctttc ttttattcat cacaattgaa ttcaaatcaa     3720
ttaacatcaa caaactttac aatcaaatta attaacaatg ttcttgaaaa atatcttgag    3780
tgttcttgct tttgctttat taattgatgc tgctccaatt gctaatgaat tgagatgtca    3840
atgtttacaa actatggctg gtattcattt gaaaaatatt caatcattga agttttgcc     3900 atcaggtcca cattgtactc aaactgaagt tattgctact ttgaaaaatg gtagagaagc    3960
ttgtttggat ccagaagctc cattggttca aaaaattgtt caaaaaatgt tgaaaggtgt    4020
tcctaaataa taaacacaac atctttgtta gataaacatt atagaaagga catgacggtc    4080
gaagatggtt taaagttaat ggatatgtgt gtcaaggaat tacaaacgag aatgcctatt    4140
gactttaaag gtgtgtacat caaggtggta gataaagatg gtataagaca gattgagtca    4200
aattgaagta gatctataag tatatatgta taatatttat gagaaactat cacttctttt    4260
aaactctaca atttgatatc tcgagtacca atatatcggt tgcaccagct ttcttcaatt    4320
cgtccattac attaccgatt tcctttctat taaccatgga tgagatggca acccagtcct    4380
cttcgtcgtc gctgtgtttg tccaaagtag agacagtagc ggcccttctg cctggagtaa    4440
tggttaaaca ttttgcttgg atggattttg gggcattgta gttacacaag acatattcct    4500
gggcagctaa acaccttga agtctttgga cgattatatt gaccatttct gggaatttac     4560
ttttctttga cgaaatcaaa tgagccgaag tctccaatat ggtttctatg gcctttaacc    4620
cagctgcttt catagtttca ccactttcaa ccaaatcgac aatagcatca gcaacaccca    4680
aggcacaaga agcctcaacg gaaccaccga catatctgat attagtaggt ttgtctgaca    4740
attgtttgaa atagtcggta ctcaattttg taaatgaaga cacaattttc tttccaacaa    4800
gctgttctgg cttttcgtac tcgccatctg ctggaacttg gatctgcaat tgcatgaac     4860 caaatttcaa atccaacaag tcctcgatgt tgtcgaattg ttcagcttct ttgatttggt    4920
ctaacccagt tataccccaag tcacaattac cttctccaac gaaaactggg atatcagctg    4980
caggcaagaa gattaatgca attggcaagt ttgtagaaag tgctatatct aatctattag    5040
atcttctaaa ctgtatatcg gcaccactca ataagttaca gcatttttcg tataatctgc    5100
```

-continued

```
ccttttagg aacagcaaat aacaaacggt ctggtaaatg attgactaaa tccattatcg      5160
gtagttggtg gttaagtaaa agaagaagtt gtgtgggaaa aatcttcacc aaaaaaaaat    5220
aaaaaatttc aatggttgcg taataatcaa aatgagtcaa ttctcacaac cgctcgcgac    5280
acgtttcaac gaaatggcct cccctaccac agaaaattaa gtacacatgt tgtgatagat    5340
tttacattta taaaaaacta ttaaataaat aaattgtctt gctgtcctat tgctttttga    5400
ctataccttc gctgtcttct tcctctgatg tcactgtatc ctcttctgtc cccaaattgt    5460
tactactaac ttctgtctcc tcatcctcca ggtacctgtc gagtcctgtg gtggattttg    5520
gggtatttat taattctccg tctaccgggg ttttcactac caaattacta ctaaccccat    5580
acccatttgg attaccatac atgtatttgt taaaccccca gttaagcaat attttgagca    5640
tatcccatgg cttgaaggat gagtagcagc acgttcctta tatgtagctt tcgacatgat    5700
ttatcttcgt ttcctgcagg ttttttgttct gtgcagttgg gttaagaata ctgggcaatt    5760
tcatgtttct tcaacactac atatgcgtat atataccaat ctaagtctgt gctccttcct    5820
tcgttcttcc ttctgttcgg agattaccga atcaaaaaaa tttcaagaaa accgaaatca    5880
aaaaaaagaa taaaaaaaaa atgatgaatt gaattgaaaa gctgtggtat ggtgcactct    5940
cagtacaatc tgctctgatg ccgcatagtt aagccagccc cgacacccgc caacacccgc    6000
tgacgcgccc tgacgggctt gtctgctccc ggcatccgct tacagacaag ctgtgaccgt    6060
ctccgggagc tgcatgtgtc agaggttttc accgtcatca ccgaaacgcg cga          6113
```

<210> SEQ ID NO 2
<211> LENGTH: 6116
<212> TYPE: DNA
<213> ORGANISM: Artificial Sequence
<220> FEATURE:
<223> OTHER INFORMATION: Synthetic construct (CXCL2 plasmid)
<220> FEATURE:
<221> NAME/KEY: misc_feature
<222> LOCATION: (2758)..(3727)
<223> OTHER INFORMATION: TDH3 promoter
<220> FEATURE:
<221> NAME/KEY: misc_feature
<222> LOCATION: (3758)..(3811)
<223> OTHER INFORMATION: SAP5 signal sequence
<220> FEATURE:
<221> NAME/KEY: misc_feature
<222> LOCATION: (3812)..(4066)
<223> OTHER INFORMATION: Codon-optimized CXCL2 ORF

<400> SEQUENCE: 2

```
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atcccctag agtcttttac atcttcggaa aacaaaaact    480 atttttctt taattcttt tttactttc tattttaat ttatatattt atattaaaaa        540
atttaaatta taattatttt tatagcacgt gatgaaaagg acccaggtgg cacttttcgg    600
ggaaatgtgc gcggaacccc tatttgttta ttttttctaaa tacattcaaa tatgtatccg    660
```

```
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atggggatc atgtaactcg ccttgatcgt    1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata cttttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc caggggggaaa cgcctggtat ctttatagtc ctgtcgggtt cgccacctc   2280
tgacttgagc gtcgattttt gtgatgctcg tcaggggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gcgcgcagta   2760
gtagtagtgg tatgatgcaa atttattgtt tgtattttt tttttgttgc tcctcgtcga   2820
caacgactgc tgattcacac caccaccacc tttgtagtca aattaaaatc gtcggtggca   2880
aaaaaaaaca cagacacaca catacagaca attgcgatat tttattttag ggtcaatttg   2940
gaacgtcacc atacagtatt cagtatgatt aatttgactt gcaaaataca aatcgcgtgg   3000
ttcaattccg aaaaattgat agtgttccat gaaaaattac aaggagagcc gtgaattata   3060
```

```
acaaatttac tcacattttg gctggcaatt tctttaaccc ccttaatttt tttcatgcag  3120
tttattattt tacgtagaag cttattctct aaacactcgg ttatccgaat atattttgct  3180
ttcagagcaa ttgactgata taataccatc aattgaataa atcagtatca tcaaatgcta  3240
gtttgagttc aataaaaggt ataatcggtg ttaactgaaa ggtattgtct aattaattag  3300
gttgcggttt ttggatcagc tgtttcaaat ccaggctcgt ggtgcacatt ttttatttt  3360 gttgtgatga ttttttcttt tctttgctta atagttagtt agtaaaatgg ataatgacgc  3420
aaaattgctt ctgaatggat gataatgccc cgggtatggc gtgtcccgta caaatcatat  3480
tatgcaaaaa tagccaaaat agacaaaaat aggtggaaat tgtttcaacc aacccactca  3540
accactaaaa tttgtcttgt caaagccaat tccaacgaaa attggatttt ttttgactta  3600
atatatatta acccttgaaa ttcccttcaa ttggaaaatt ttttttaattt atttatttct  3660 tctttctttt tttcttttc ttttcttc ttttattcat cacaattgaa ttcaaatcaa  3720
ttaacatcaa caaactttac aatcaaatta attaacaatg ttcttgaaaa atatcttgag  3780
tgttcttgct tttgctttat taattgatgc tgctgttgtt gcttcagaat tgagatgtca  3840
atgtttgaaa actttgccaa gagttgattt caaaaatatt caatcattgt cagttactcc  3900
accaggtcca cattgtgctc aaactgaagt tattgctact ttgaaaggtg gtcaaaaagt  3960
ttgtttggat ccagaagctc cattggttca aaaaattatt caaaaatttt taaataaagg  4020
taaagctaat tgatgaacac aacatctttg ttagataaac attatagaaa ggacatgacg  4080
gtcgaagatg gtttaaagtt aatggatatg tgtgtcaagg aattcaaaac gagaatgcct  4140 attgactta aaggtgtgta catcaaggtg gtagataaag atggtataag acagattgag  4200
tcaaattgaa gtagatctat aagtatatat gtataatatt tatgagaaac tatcacttct  4260
tttaaactct acaatttgat atctcgagta ccaatatatc ggttgcacca gctttcttca  4320
attcgtccat tacattaccg atttcctttc tattaaccat ggatgagatg gcaacccagt  4380
cctcttcgtc gtcgctgtgt tgtccaaag tagagacagt agcggccctt ctgcctggag  4440
taatggttaa acattttgct tggatggatt ttggggcatt gtagttacac aagacatatt  4500
cctgggcagc taaaacacct tgaagtcttt ggacgattat attgaccatt tctgggaatt  4560
tacttttctt tgacgaaatc aaatgagccg aagtctccaa tatggtttct atggcctta  4620 acccagctgc tttcatagtt tcaccacttt caaccaaatc gacaatagca tcagcaacac  4680
ccaaggcaca agaagcctca acggaaccac cgacatatct gatattagta ggtttgtctg  4740
acaattgttt gaaatagtcg gtactcaatt ttgtaaatga agacacaatt ttcttcaa  4800 caagctgttc tggcttttcg tactcgccat ctgctggaac ttggatctgc aatttgcatg  4860
aaccaaattt caaatccaac aagtcctcga tgttgtcgaa ttgttcagct tctttgattt  4920
ggtctaaccc agttataccc aagtcacaat taccttctcc aacgaaaact gggatatcag  4980
ctgcaggcaa aagattaat gcaattggca agtttgtaga aagtgctata tctaatctat  5040
tagatcttct aaactgtata tcggcaccac tcaataagtt acagcatttt tcgtataatc  5100
tgcccttttt aggaacagca aataacaaac ggtctggtaa atgattgact aaatccatta  5160
tcggtagttg gtggttaagt aaaagaagaa gttgtgtggg aaaaatcttc accaaaaaaa  5220
aataaaaaat ttcaatggtt gcgtaataat caaaatgagt caattctcac aaccgctcgc  5280
gacacgtttc aacgaaatgg cctcccctac cacagaaaat taagtacaca tgttgtgata  5340 gatttacat ttataaaaaa ctattaaata aataaattgt cttgctgtcc tattgctttt  5400
```

-continued

| | |
|---|---|
| tgactatacc ttcgctgtct tcttcctctg atgtcactgt atcctcttct gtccccaaat | 5460 |
| tgttactact aacttctgtc tcctcatcct ccaggtacct gtcgagtcct gtggtggatt | 5520 |
| ttggggtatt tattaattct ccgtctaccg gggttttcac taccaaatta ctactaaccc | 5580 |
| catacccatt tggattacca tacatgtatt tgttaaaccc ccagttaagc aatattttga | 5640 |
| gcatatccca tggcttgaag gatgagtagc agcacgttcc ttatatgtag ctttcgacat | 5700 |
| gatttatctt cgtttcctgc aggtttttgt tctgtgcagt tgggttaaga atactgggca | 5760 |
| atttcatgtt tcttcaacac tacatatgcg tatatatacc aatctaagtc tgtgctcctt | 5820 |
| ccttcgttct tccttctgtt cggagattac cgaatcaaaa aaatttcaaa gaaaccgaaa | 5880 |
| tcaaaaaaaa gaataaaaaa aaaatgatga attgaattga aaagctgtgg tatggtgcac | 5940 |
| tctcagtaca atctgctctg atgccgcata gttaagccag ccccgacacc cgccaacacc | 6000 |
| cgctgacgcg ccctgacggg cttgtctgct cccggcatcc gcttacagac aagctgtgac | 6060 |
| cgtctccggg agctgcatgt gtcagaggtt ttcaccgtca tcaccgaaac gcgcga | 6116 |

<210> SEQ ID NO 3
<211> LENGTH: 6173
<212> TYPE: DNA
<213> ORGANISM: Artificial Sequence
<220> FEATURE:
<223> OTHER INFORMATION: Synthetic construct (CXCL5 plasmid)
<220> FEATURE:
<221> NAME/KEY: misc_feature
<222> LOCATION: (2758)..(3727)
<223> OTHER INFORMATION: TDH3 promoter
<220> FEATURE:
<221> NAME/KEY: misc_feature
<222> LOCATION: (3758)..(3811)
<223> OTHER INFORMATION: SAP5 signal sequence
<220> FEATURE:
<221> NAME/KEY: misc_feature
<222> LOCATION: (3812)..(4123)
<223> OTHER INFORMATION: Codon-optimized CXCL5 ORF

<400> SEQUENCE: 3

| | |
|---|---|
| gacgaaaggg cctcgtgata cgcctatttt tataggttaa tgtcatgata ataatggttt | 60 |
| cttaggacgg atcgcttgcc tgtaacttac acgcgcctcg tatcttttaa tgatggaata | 120 |
| atttgggaat ttactctgtg tttatttatt tttatgtttt gtatttggat tttagaaagt | 180 |
| aaataaagaa ggtagaagag ttacggaatg aagaaaaaaa aataaacaaa ggtttaaaaa | 240 |
| atttcaacaa aaagcgtact ttacatatat atttattaga caagaaaagc agattaaata | 300 |
| gatatacatt cgattaacga taagtaaaat gtaaaatcac aggattttcg tgtgtggtct | 360 |
| tctacacaga caagatgaaa caattcggca ttaatacctg agagcaggaa gagcaagata | 420 |
| aaaggtagta tttgttggcg atccccctag agtcttttac atcttcggaa aacaaaaact | 480 |
| attttttctt taatttcttt ttttactttc tatttttaat ttatatattt atattaaaaa | 540 |
| atttaaatta taattatttt tatagcacgt gatgaaaagg acccaggtgg cacttttcgg | 600 |
| ggaaatgtgc gcggaacccc tatttgttta ttttctaaa tacattcaaa tatgtatccg | 660 |
| ctcatgagac aataaccctg ataaatgctt caataatatt gaaaaaggaa gagtatgagt | 720 |
| attcaacatt tccgtgtcgc ccttattccc ttttttgcgg cattttgcct tcctgttttt | 780 |
| gctcacccag aaacgctggt gaaagtaaaa gatgctgaag atcagttggg tgcacgagtg | 840 |
| ggttacatcg aactggatct caacagcggg aagatccttg agagttttcg ccccgaagaa | 900 |
| cgttttccaa tgatgagcac ttttaaagtt ctgctatgtg gcgcggtatt atcccgtatt | 960 |
| gacgccgggc aagagcaact cggtcgccgc atacactatt ctcagaatga cttggttgag | 1020 |

```
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atggggggatc atgtaactcg ccttgatcgt   1200
tgggaaccgg agctgaatga agccatacca acgacgagc gtgacaccac gatgcctgta    1260
gcaatggcaa caacgttgcg caaactatta actggcgaac tacttactct agcttcccgg   1320
caacaattaa tagactggat ggaggcggat aaagttgcag gaccacttct cgctcggcc    1380 cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata tactttagat tgatttaaaa   1620 cttcatttt aatttaaaag gatctaggtg aagatccttt ttgataatct catgaccaaa    1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctcttttcc gaaggtaact    1860 ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg gttcgtgca cacagcccag cttggagcga    2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc caggggggaaa cgcctggtat ctttatagtc ctgtcgggtt tcgccacctc   2280
tgacttgagc gtcgattttt gtgatgctcg tcagggggc ggagcctatg gaaaaacgcc    2340
agcaacgcgg ccttttacg gttcctggcc ttttgctggc cttttgctca catgttcttt    2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gcgcgcagta   2760
gtagtagtgg tatgatgcaa atttattgtt tgtatttttt ttttgttgc tcctcgtcga    2820 caacgactgc tgattcacac caccaccacc tttgtagtca aattaaaatc gtcggtggca   2880
aaaaaaaaca cagacacaca catacagaca attgcgatat tttattttag ggtcaatttg   2940
gaacgtcacc atacagtatt cagtatgatt aatttgactt gcaaaataca aatcgcgtgg   3000
ttcaattccg aaaaattgat agtgttccat gaaaaattac aaggagagcc gtgaattata   3060
acaaatttac tcacattttg gctggcaatt tctttaaccc ccttaatttt tttcatgcag   3120
tttattattt tacgtagaag cttattctct aaacactcgg ttatccgaat atattttgct   3180
ttcagagcaa ttgactgata taataccatc aattgaataa atcagtatca tcaaatgcta   3240
gtttgagttc aataaaaggt ataatcggtg ttaactgaaa ggtattgtct aattaattag   3300
gttgcggttt ttggatcagc tgtttcaaat ccaggctcgt ggtgcacatt ttttattttt   3360
```

-continued

```
gttgtgatga ttttttcttt tctttgctta atagttagtt agtaaaatgg ataatgacgc    3420
aaaattgctt ctgaatggat gataatgccc cgggtatggc gtgtcccgta caaatcatat    3480
tatgcaaaaa tagccaaaat agacaaaaat aggtggaaat tgtttcaacc aacccactca    3540
accactaaaa tttgtcttgt caaagccaat tccaacgaaa attggatttt ttttgactta    3600
atatatatta acccttgaaa ttcccttcaa ttggaaaatt tttttaattt atttatttct    3660
tctttctttt tttcttttc ttttctttc tttattcat cacaattgaa ttcaaatcaa       3720
ttaacatcaa caaactttac aatcaaatta attaacaatg ttcttgaaaa atatcttgag    3780
tgttcttgct tttgctttat taattgatgc tgctccatca tcagttattg ctgctactga    3840
attgagatgt gtttgtttga ctgttactcc aaaaattaat ccaaaattga ttgctaattt    3900
ggaagttatt ccagctggtc cacaatgtcc aactgttgaa gttattgcta aattgaaaaa    3960
tcaaaagaa gtttgtttgg atccagaagc tccagttatt aaaaaaatta ttcaaaaaat     4020
tttgggttca gataaaaaaa aagctaaaag aaatgctttg gctgttgaaa gaactgcttc    4080
agttcaatag tagacacaac atctttgtta gataaacatt atagaaagga catgacggtc    4140
gaagatggtt taaagttaat ggatatgtgt gtcaaggaat tacaaacgag aatgcctatt    4200
gactttaaag gtgtgtacat caaggtggta gataaagatg gtataagaca gattgagtca    4260
aattgaagta gatctataag tatatatgta taatatttat gagaaactat cacttctttt    4320
aaactctaca atttgatatc tcgagtacca atatatcggt tgcaccagct ttcttcaatt    4380
cgtccattac attaccgatt tcctttctat taaccatgga tgagatggca acccagtcct    4440
cttcgtcgtc gctgtgtttg tccaaagtag agacagtagc ggcccttctg cctggagtaa    4500
tggttaaaca ttttgcttgg atggattttg gggcattgta gttacacaag acatattcct    4560
gggcagctaa acaccttga agtctttgga cgattatatt gaccatttct gggaatttac     4620
ttttctttga cgaaatcaaa tgagccgaag tctccaatat ggtttctatg gcctttaacc    4680
cagctgcttt catagtttca ccactttcaa ccaaatcgac aatagcatca gcaacaccca    4740
aggcacaaga agcctcaacg gaaccaccga catatctgat attagtaggt ttgtctgaca    4800
attgttgaa atagtcggta ctcaattttg taaatgaaga cacaattttc tttccaacaa     4860
gctgttctgg cttttcgtac tcgccatctg ctggaacttg gatctgcaat ttgcatgaac    4920
caaatttcaa atccaacaag tcctcgatgt tgtcgaattg ttcagcttct ttgatttggt    4980
ctaacccagt tatacccaag tcacaattac cttctccaac gaaaactggg atatcagctg    5040
caggcaagaa gattaatgca attggcaagt ttgtagaaag tgctatatct aatctattag    5100
atcttctaaa ctgtatatcg gcaccactca ataagttaca gcattttcg tataatctgc     5160
cctttttagg aacagcaaat aacaaacggt ctggtaaatg attgactaaa tccattatcg    5220
gtagttggtg gttaagtaaa agaagaagtt gtgtgggaaa atcttcacc aaaaaaaat     5280
aaaaatttc aatggttgcg taataatcaa aatgagtcaa ttctcacaac cgctcgcgac    5340
acgtttcaac gaaatggcct cccctaccac agaaaattaa gtacacatgt tgtgatagat    5400
tttacattta taaaaaacta ttaaataaat aaattgtctt gctgtcctat tgcttttga    5460
ctataccttc gctgtcttct tcctctgatg tcactgtatc ctcttctgtc cccaaattgt    5520
tactactaac ttctgtctcc tcatcctcca ggtacctgtc gagtcctgtg gtggattttg    5580
gggtatttat taattctccg tctaccgggg ttttcactac caaattacta ctaacccccat   5640
acccatttgg attaccatac atgtatttgt taaaccccca gttaagcaat attttgagca    5700
tatcccatgg cttgaaggat gagtagcagc acgttcctta tatgtagctt tcgacatgat    5760
```

```
ttatcttcgt ttcctgcagg ttttttgttct gtgcagttgg gttaagaata ctgggcaatt    5820
tcatgtttct tcaacactac atatgcgtat atataccaat ctaagtctgt gctccttcct    5880
tcgttcttcc ttctgttcgg agattaccga atcaaaaaaa tttcaaagaa accgaaatca    5940
aaaaaaagaa taaaaaaaaa atgatgaatt gaattgaaaa gctgtggtat ggtgcactct    6000
cagtacaatc tgctctgatg ccgcatagtt aagccagccc cgacacccgc caacacccgc    6060
tgacgcgccc tgacgggctt gtctgctccc ggcatccgct tacagacaag ctgtgaccgt    6120
ctccgggagc tgcatgtgtc agaggttttc accgtcatca ccgaaacgcg cga           6173
```

<210> SEQ ID NO 4
<211> LENGTH: 6296
<212> TYPE: DNA
<213> ORGANISM: Artificial Sequence
<220> FEATURE:
<223> OTHER INFORMATION: Synthetic construct (IL17A plasmid)
<220> FEATURE:
<221> NAME/KEY: misc_feature
<222> LOCATION: (2758)..(3727)
<223> OTHER INFORMATION: TDH3 promoter
<220> FEATURE:
<221> NAME/KEY: misc_feature
<222> LOCATION: (3758)..(3811)
<223> OTHER INFORMATION: SAP5 signal sequence
<220> FEATURE:
<221> NAME/KEY: misc_feature
<222> LOCATION: (3812)..(4246)
<223> OTHER INFORMATION: Codon-optmized IL-17A ORF

<400> SEQUENCE: 4

```
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atcccccctag agtcttttac atcttcggaa aacaaaaact    480
atttttcctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg catttgcct tcctgttttt    780 gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
```

```
gcaatggcaa caacgttgcg caaactatta actggcgaac tacttactct agcttcccgg      1320
caacaattaa tagactggat ggaggcggat aaagttgcag gaccacttct gcgctcggcc      1380
cttccggctg gctggtttat tgctgataaa tctggagccg gtgagcgtgg gtctcgcggt      1440
atcattgcag cactggggcc agatggtaag ccctcccgta tcgtagttat ctacacgacg      1500
gggagtcagg caactatgga tgaacgaaat agacagatcg ctgagatagg tgcctcactg      1560
attaagcatt ggtaactgtc agaccaagtt tactcatata tactttagat tgatttaaaa      1620
cttcattttt aatttaaaag gatctaggtg aagatccttt ttgataatct catgaccaaa      1680
atcccttaac gtgagttttc gttccactga gcgtcagacc ccgtagaaaa gatcaaagga      1740
tcttcttgag atcctttttt tctgcgcgta atctgctgct tgcaaacaaa aaaaccaccg      1800
ctaccagcgg tggtttgttt gccggatcaa gagctaccaa ctcttttttcc gaaggtaact      1860 ggcttcagca gagcgcagat accaaatact gtccttctag tgtagccgta gttaggccac      1920
cacttcaaga actctgtagc accgcctaca tacctcgctc tgctaatcct gttaccagtg      1980
gctgctgcca gtggcgataa gtcgtgtctt accgggttgg actcaagacg atagttaccg      2040
gataaggcgc agcggtcggg ctgaacgggg ggttcgtgca cacagcccag cttggagcga      2100
acgacctaca ccgaactgag atacctacag cgtgagctat gagaaagcgc cacgcttccc      2160
gaagggagaa aggcggacag gtatccggta agcggcaggg tcggaacagg agagcgcacg      2220
agggagcttc caggggggaaa cgcctggtat ctttatagtc ctgtcgggtt cgccacctc      2280 tgacttgagc gtcgattttt gtgatgctcg tcagggggggc ggagcctatg gaaaaacgcc      2340
agcaacgcgg cctttttacg gttcctggcc ttttgctggc cttttgctca catgttcttt      2400
cctgcgttat cccctgattc tgtggataac cgtattaccg cctttgagtg agctgatacc      2460
gctcgccgca gccgaacgac cgagcgcagc gagtcagtga gcgaggaagc ggaagagcgc      2520
ccaatacgca aaccgcctct ccccgcgcgt tggccgattc attaatgcag ctggcacgac      2580
aggtttcccg actggaaagc gggcagtgag cgcaacgcaa ttaatgtgag ttacctcact      2640
cattaggcac cccaggcttt acactttatg cttccggctc ctatgttgtg tggaattgtg      2700
agcggataac aatttcacac aggaaacagc tatgaccatg attacgccaa gcgcgcagta      2760
gtagtagtgg tatgatgcaa atttattgtt tgtattttt tttttgttgc tcctcgtcga      2820
caacgactgc tgattcacac caccaccacc tttgtagtca aattaaaatc gtcggtggca      2880
aaaaaaaaca cagacacaca catacagaca attgcgatat tttatttag ggtcaatttg      2940 gaacgtcacc atacagtatt cagtatgatt aatttgactt gcaaaataca aatcgcgtgg      3000
ttcaattccg aaaaattgat agtgttccat gaaaaattac aaggagagcc gtgaattata      3060
acaaatttac tcacattttg gctggcaatt tcttttaaccc ccttaatttt tttcatgcag      3120
tttattattt tacgtagaag cttattctct aaacactcgg ttatccgaat atattttgct      3180
ttcagagcaa ttgactgata taataccatc aattgaataa atcagtatca tcaaatgcta      3240
gtttgagttc aataaaaggt ataatcggtg ttaactgaaa ggtattgtct aattaattag      3300
gttgcggttt ttggatcagc tgtttcaaat ccaggctcgt ggtgcacatt ttttattttt      3360
gttgtgatga tttttttcttt tctttgctta atagttagtt agtaaaatgg ataatgacgc      3420
aaaattgctt ctgaatggat gataatgccc cgggtatggc gtgtcccgta caaatcatat      3480
tatgcaaaaa tagccaaaat agacaaaaat aggtggaaat tgtttcaacc aacccactca      3540
accactaaaa tttgtcttgt caaagccaat tccaacgaaa attggatttt ttttgactta      3600
atatatatta acccttgaaa ttcccttcaa ttggaaaatt ttttaatttt atttatttct      3660
```

```
tctttcttttt tttcttttttc ttttttctttc tttattcat cacaattgaa ttcaaatcaa    3720
ttaacatcaa caaactttac aatcaaatta attaacaatg ttcttgaaaa atatcttgag    3780
tgttcttgct tttgctttat taattgatgc tgctgctatt attccacaat catcagcttg    3840
tccaaatact gaagctaaag atttcttgca aaatgttaaa gttaatttga aagttttcaa    3900
ttcattgggt gctaaagttt catcaagaag accatcagat tatttgaata gatcaacttc    3960
accatggaca ttgcatagaa atgaagatcc agatagatat ccatcagtta tttgggaagc    4020
tcaatgtaga catcaaagat gtgttaatgc tgaaggtaaa ttggatcatc atatgaattc    4080
agttttgatt caacaagaaa ttttggtttt gaaaagagaa ccagaatctt gtccattcac    4140
tttcagagtt gaaaaaatgt tggttggtgt tggttgtact tgtgttgctt caattgttag    4200
acaagctgct aataaacac aacatctttg ttagataaac attatagaaa ggacatgacg    4260
gtcgaagatg gtttaaagtt aatggatatg tgtgtcaagg aattacaaac gagaatgcct    4320
attgacttta aggtgtgta catcaaggtg gtagataaag atggtataag acagattgag    4380
tcaaattgaa gtagatctat aagtatatat gtataatatt tatgagaaac tatcacttct    4440
tttaaactct acaatttgat atctcgagta ccaatatatc ggttgcacca gctttcttca    4500
attcgtccat tacattaccg atttcctttc tattaaccat ggatgagatg caacccagt    4560 cctcttcgtc gtcgctgtgt ttgtccaaag tagagacagt agcggccctt ctgcctggag    4620
taatggttaa acattttgct tggatggatt ttggggcatt gtagttacac aagacatatt    4680
cctgggcagc taaacacct tgaagtcttt ggacgattat attgaccatt tctgggaatt    4740 tactttctctt tgacgaaatc aaatgagccg aagtctccaa tatggtttct atggccttta    4800
acccagctgc tttcatagtt tcaccacttt caaccaaatc gacaatagca tcagcaacac    4860
ccaaggcaca agaagcctca acggaaccac cgacatatct gatattagta ggtttgtctg    4920
acaattgttt gaaatagtcg gtactcaatt ttgtaaatga agacacaatt ttctttccaa    4980
caagctgttc tggcttttcg tactcgccat ctgctggaac ttggatctgc aatttgcatg    5040
aaccaaattt caaatccaac aagtcctcga tgttgtcgaa ttgttcagct tctttgattt    5100
ggtctaaccc agttataccc aagtcacaat taccttctcc aacgaaaact gggatatcag    5160
ctgcaggcaa gaagattaat gcaattggca agtttgtaga aagtgctata tctaatctat    5220
tagatcttct aaactgtata tcggcaccac tcaataagtt acagcatttt tcgtataatc    5280 tgccctttt aggaacagca ataacaaac ggtctggtaa atgattgact aaatccatta    5340
tcggtagttg gtggtaagt aaaagaagaa gttgtgtggg aaaaatcttc accaaaaaaa    5400 aataaaaat ttcaatggtt gcgtaataat caaaatgagt caattctcac aaccgctcgc    5460
gacacgtttc aacgaaatgg cctcccctac cacagaaaat taagtacaca tgttgtgata    5520
gattttacat ttataaaaaa ctattaaata aataaattgt cttgctgtcc tattgctttt    5580
tgactatacc ttcgctgtct tcttcctctg atgtcactgt atcctcttct gtccccaaat    5640
tgttactact aacttctgtc tcctcatcct ccaggtacct gtcgagtcct gtggtggatt    5700
ttggggtatt tattaattct ccgtctaccg gggttttcac taccaaatta ctactaaccc    5760
catacccatt tggattacca tacatgtatt tgttaaaccc ccagttaagc aatatttga    5820 gcatatccca tggcttgaag gatgagtagc agcacgttcc ttatatgtag ctttcgacat    5880
gatttatctt cgtttcctgc aggttttgt tctgtgcagt tgggtaaga atactgggca    5940 atttcatgtt tcttcaacac tacatatgcg tatatatacc aatctaagtc tgtgctcctt    6000
```

```
cctttcgttct tccttctgtt cggagattac cgaatcaaaa aaatttcaaa gaaaccgaaa    6060
tcaaaaaaaa gaataaaaaa aaaatgatga attgaattga aaagctgtgg tatggtgcac    6120
tctcagtaca atctgctctg atgccgcata gttaagccag ccccgacacc cgccaacacc    6180
cgctgacgcg ccctgacggg cttgtctgct cccggcatcc gcttacagac aagctgtgac    6240
cgtctccggg agctgcatgt gtcagaggtt ttcaccgtca tcaccgaaac gcgcga         6296

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
gctatgacca tgattacgcc                                                  20

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
tataatgttt atctaacaaa gatgttgtgt                                       30

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
gataatgacg caaaattgct tct                                              23

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gctatgacca tgattacgcc                                                  20

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 9
tataatgttt atctaacaaa gatgttgtgt                                       30
```